(12) United States Patent
Liu

(10) Patent No.: US 12,371,817 B2
(45) Date of Patent: Jul. 29, 2025

(54) METHODS OF MAKING AND UTILIZING AMBER-OBLIGATED PHAGE DISPLAY LIBRARIES

(71) Applicant: The Texas A&M University System, College Station, TX (US)

(72) Inventor: Wenshe Liu, College Station, TX (US)

(73) Assignee: The Texas A&M University System, College Station, TX (US)

( * ) Notice: Subject to any disclaimer, the term of this patent is extended or adjusted under 35 U.S.C. 154(b) by 646 days.

(21) Appl. No.: 17/436,494

(22) PCT Filed: Mar. 4, 2020

(86) PCT No.: PCT/US2020/020961
§ 371 (c)(1),
(2) Date: Sep. 3, 2021

(87) PCT Pub. No.: WO2020/180971
PCT Pub. Date: Sep. 10, 2020

(65) Prior Publication Data
US 2022/0259585 A1      Aug. 18, 2022

Related U.S. Application Data

(60) Provisional application No. 62/813,340, filed on Mar. 4, 2019.

(51) Int. Cl.
*C40B 50/06*     (2006.01)
*C12N 15/10*     (2006.01)

(52) U.S. Cl.
CPC .......... *C40B 50/06* (2013.01); *C12N 15/1037* (2013.01)

(58) Field of Classification Search
None
See application file for complete search history.

(56) References Cited

U.S. PATENT DOCUMENTS

| 5,770,356 A | 6/1998 | Light, II et al. |
| 5,925,559 A | 7/1999 | Collins et al. |

(Continued)

FOREIGN PATENT DOCUMENTS

| AU | 2007251897 | 1/2008 |
| WO | 02086075 A2 | 10/2002 |
| WO | WO-2012/023285 A1 | 2/2012 |

OTHER PUBLICATIONS

Wang, Lei et al.; "Expanding the Genetic Code"; Angewante Chemie International Edition; vol. 44; 2005; pp. 34-66.

(Continued)

*Primary Examiner* — Christian C Boesen
(74) *Attorney, Agent, or Firm* — Winstead PC

(57) ABSTRACT

Embodiments of the present disclosure pertain to methods of constructing a phage display library where at least 90% of combinatorial regions in the phage display library include at least one inframe amber codon. Further embodiments of the present disclosure pertain to the formed phage display libraries. Additional embodiments of the present disclosure pertain to methods of selecting peptides or proteins that bind to a desired target (e.g., a ligand binding site of a desired target) by utilizing the phage display libraries of the present disclosure. Further embodiments of the present disclosure pertain to peptides that have been screened from the phage display libraries and methods of the present disclosure, such as inhibitors of sirtuin 2, or inhibitors of ENL.

4 Claims, 12 Drawing Sheets
Specification includes a Sequence Listing.

(56) References Cited

U.S. PATENT DOCUMENTS

| | | |
|---|---|---|
| 2003/0148263 A1 | 8/2003 | Larocca et al. |
| 2009/0017521 A1 | 1/2009 | Houtzager et al. |
| 2009/0137424 A1 | 5/2009 | Tsao et al. |
| 2016/0341743 A1 | 11/2016 | Ruthenburg et al. |
| 2017/0355980 A1 | 12/2017 | Ladner et al. |

OTHER PUBLICATIONS

Tian, Feng et al.; "A Phage Display Syustem with Unnatural Amino Acids"; Journal of the American Chemical Society; vol. 126; Jul. 1, 2004; pp. 15962-15963.

Wals, Kim et al.; "Unnatural amino acid incorporation in *E. coli*: current and future applications in the design of therapeutic proteins"; Frontiers in Chemistry; vol. 2 Art. 15; Apr. 2014; 12 pages.

Tharp, Jeffery M. et al.; "An amber obligate active site-directed ligand evolution technique for phage display"; Nature Communications; vol. 11; Mar. 13, 2020; 14 pages.

"CM13 Interference—Resistant Helper Phage"; Antibody Design Laboratories; Instructional Manual Version A1.6; Jun. 2016; 7 pages.

```
5'                                                    3'
...T C G T T G T A G T T G C A G C A T T C T...
...T A G A G T G C T A T T A C G T A T T G T...
...A T T T A G A T T C A T C C G T A T T T T...
...T A T A G T A T T A A G T G G T A G G T T...
...G G T G C G T A G A G G C C G G G G A T G...
...C G T A T G C A T T A G G C G T T T T T T...
...A C T A C T T A T A C T G G T G A T T A G...
...G G T T C G T T G C A T G T T C A T T A G...
...T A G T T G C A T C C G G G G A T G C G T...
...T A T T A G A C T G A T T C T G A T G C T...
```

AMINO ACID SEQUENCE

| CLONE | 1 | 2 | 3 | 4 | 5 | 6 | 7 |
|---|---|---|---|---|---|---|---|
| | *THIRD SELECTION ROUND* | | | | | | |
| SAP01 | K | X | N | F | G | Y | Y |
| SAP02 | K | W | K | V | X | T | S |
| SAP03 | T | W | X | K | S | N | W |
| SAP04 | M | A | K | P | Q | R | X |
| SAP05 | R | E | H | K | P | X | N |
| SAP06 | K | L | X | K | H | Y | P |

| CLONE | 1 | 2 | 3 | 4 | 5 | 6 | 7 |
|---|---|---|---|---|---|---|---|
| | *FOURTH SELECTION ROUND* | | | | | | |
| SAP09 | K | L | X | K | H | Y | P |
| SAP10 | K | L | X | K | H | Y | P |
| SAP11 | K | L | X | K | H | Y | P |
| SAP12 | K | L | X | K | H | Y | P |
| SAP13 | K | H | X | K | A | I | P |
| SAP14 | K | M | X | P | Q | R | N |
| SAP15 | K | M | X | P | Q | R | N |
| SAP16 | K | M | X | P | Q | R | N |
| SAP17 | K | M | X | P | Q | R | N |
| SAP18 | K | M | X | P | Q | R | N |
| SAP19 | K | C | X | N | C | R | |
| SAP20 | S | A | A | K | T | X | I |

*FIG. 5A*

AMINO ACID SEQUENCE    ncAA = X

| CLONE | -6 | -5 | -4 | -3 | -2 | -1 | 0 | 1 | 2 | 3 | 4 | 5 | 6 |
|---|---|---|---|---|---|---|---|---|---|---|---|---|---|
| S2P01 | | | | | | L | X | M | T | S | I | L | |
| S2P02 | | | | | H | L | X | T | F | F | Y | | |
| S2P03 | | | | C | T | V | X | T | S | L | | | |
| S2P04 | | | T | C | T | V | X | I | G | | | | |
| S2P05 | | | T | C | T | V | X | I | G | | | | |
| S2P06 | | | T | C | T | V | X | I | G | | | | |
| S2P07 | | | | C | T | F | X | V | P | T | | | |
| S2P08 | | | W | S | G | F | X | A | P | | | | |
| S2P09 | | | W | S | G | F | X | A | P | | | | |
| S2P10 | | | | | | F | X | L | E | S | F | L | |
| S2P11 | | | S | N | V | F | X | V | I | | | | |
| S2P12 | | | | | A | F | X | H | M | T | V | | |
| S2P13 | | | | Q | M | R | F | X | P | I | | | |
| S2P14 | | | | Q | M | R | F | X | P | I | | | |
| S2P15 | | | | | | | X | V | C | S | C | Y | A |
| S2P16 | | | | | | | X | V | C | S | C | Y | A |
| S2P17 | | | C | W | W | C | X | V | S | | | | |
| S2P18 | | | T | E | S | N | H | X | G | | | | |
| S2P19 | L | F | L | W | M | P | X | | | | | | |
| S2P20 | | | | | S | P | M | X | N | K | V | | |

*FIG. 5B*

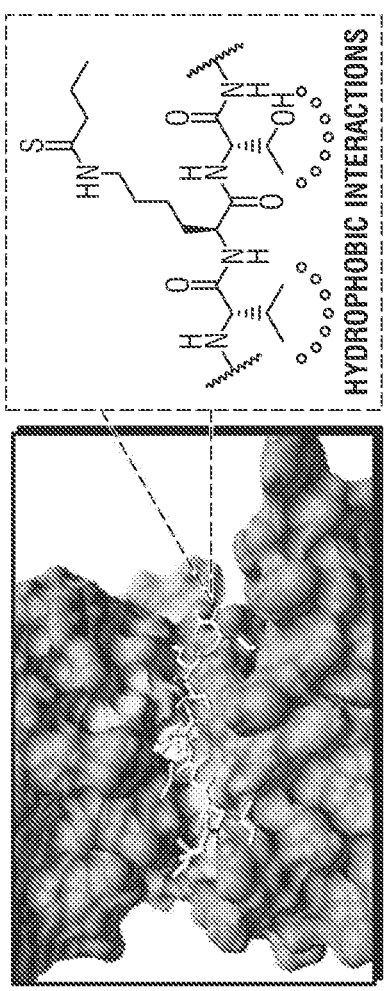
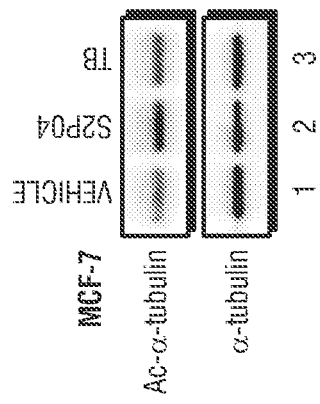
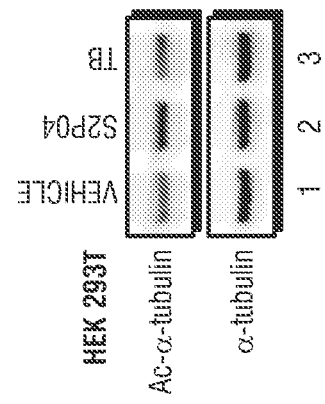
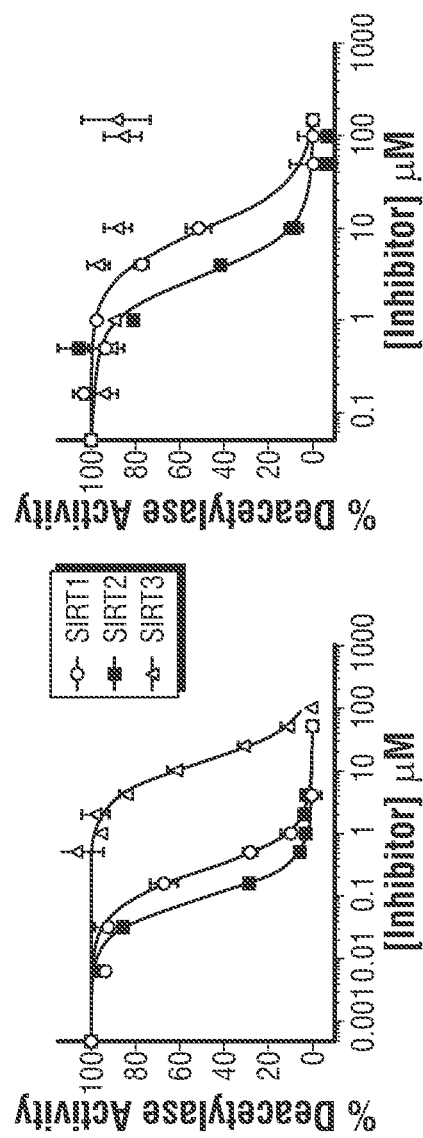
FIG. 6A
FIG. 6B
FIG. 6C

| LIGAND | SEQUENCE[a] | % SEQ. R1 | % SEQ. R4 | ENRICH RATIO | Kd (nM) |
|---|---|---|---|---|---|
| 7CrkEnl1 | DIWCFXG | 0.15 | 80.44 | 536 | 94 |
| 7CrkEnl2 | SXDIWCF | 0.06 | 17.99 | 300 | 90 |

[a] X DENOTES CrK

| COMPOUND | STRUCTURE | IC$_{50}$ (nM) |
|---|---|---|
| TB | (structure shown) | 3,108 ± 45 |
| S2P03 | H$_2$N—C-T-V-X-T-S-L—NH$_2$ | 68 ± 5 |
| S2P04 | H$_2$N—T-C-T-V-X-I-G—NH$_2$ | 92 ± 3 |
| S2P07 | H$_2$N—C-T-F-X-V-P-T—NH$_2$ | 101 ± 13 |
| S2P04-5 | H$_2$N—C-T-V-X-I—NH$_2$ | 136 ± 29 |
| Ac-S2P04-5 | Ac—C-T-V-X-I—NH$_2$ | 191 ± 9 |
| S2P04(Abu)-5 | H$_2$N—Abu-T-V-X-I—NH$_2$ | 119 ± 3 |

FIG. 9

METHODS OF MAKING AND UTILIZING AMBER-OBLIGATED PHAGE DISPLAY LIBRARIES

CROSS-REFERENCE TO RELATED APPLICATIONS

This application claims priority to U.S. Provisional Patent Application No. 62/813,340, filed on Mar. 4, 2019. The entirety of the aforementioned application is incorporated herein by reference.

STATEMENT REGARDING FEDERALLY SPONSORED RESEARCH

This invention was made with government support under Grant No. R01CA161158, awarded by National Institutes of Health. The government has certain rights in the invention.

The development of this invention was funded in part by the Welch Foundation under grant number A-1715.

BACKGROUND

Phage display technologies have numerous limitations, including limited abilities to combine phage display and chemical modification in generating peptide libraries, and incorporating non-canonical amino acids in a cell-surface display. Various embodiments of the present disclosure address the aforementioned limitations.

SUMMARY

In some embodiments, the present disclosure pertains to methods of constructing a phage display library by: (a) providing a naïve phage display library, where the naïve phage display library includes a plurality of nucleic acids, where the plurality of nucleic acids include nucleic acids with a phage coat protein gene with a combinatorial region, and where the combinatorial regions of at least some of the nucleic acids include at least one in-frame amber codon; (b) transforming the naïve phage display library into bacterial host cells; (c) inducing expression of the phage coat protein gene in the transformed bacterial host cells, where the expression of the phage coat protein from nucleic acids that only contain in-frame sense codons in the phage coat protein gene render the bacterial host cells immune to infection by a helper phage; (d) infecting the transformed bacterial host cells with the helper phage, where the helper phage encodes and expresses a gene that renders the infected bacteria resistant to an antibiotic; (e) growing the infected and uninfected bacterial host cells in a medium containing the antibiotic, where the growing results in the selection of the infected bacteria, and where the infected bacteria include the helper phage and at least some of the nucleic acids with the phage coat protein gene with the at least one in-frame amber codon in the combinatorial region; (f) extracting the nucleic acids from the bacterial cell host cells; (g) transforming the extracted nucleic acids into amber-suppressing bacterial host strains, where the amber-suppressing bacterial host strains are co-infected with a knockout helper phage that does not express the phage coat protein gene, and where the transforming allows for the selective production of phage particles from cells harboring nucleic acids with the phage coat protein gene with the at least one in-frame amber codon in the combinatorial region; and (h) purifying the nucleic acids from the produced phage particles to provide the phage display library, where at least 90% of the combinatorial regions in the phage display library include at least one in-frame amber codon.

Additional embodiments of the present disclosure pertain to phage display libraries that include a plurality of nucleic acids. The plurality of nucleic acids include nucleic acids with a phage coat protein gene that includes a combinatorial region, where at least 90% of the combinatorial regions in the phage display library include at least one in-frame amber codon. Further embodiments of the present disclosure pertain to methods of selecting peptides or proteins that bind to a desired target by: (a) providing a phage display library of the present disclosure; (b) transforming the phage display library into bacterial host cells, where the bacterial host cells are capable of translating the combinatorial region of the phage coat protein gene such that the at least one in-frame amber codon encodes a desired non-canonical amino acid, where the bacterial host cells are co-infected with a knockout helper phage that does not express the phage coat protein gene, and where the transforming allows for the production of phage particles that contain the phage coat protein with the desired non-canonical amino acid in the combinatorial region; (c) screening the phage particles against the desired target, where the screening results in the selection of phage particles with phage coat protein combinatorial regions that bind to the desired target; and (d) identifying the amino acid sequences of the combinatorial regions of the selected phage particles.

Additional embodiments of the present disclosure pertain to methods of selecting peptides that bind to a ligand binding site of a desired target by: (a) providing a phage display library with a plurality of nucleic acids, where the plurality of nucleic acids include nucleic acids with a phage coat protein gene that includes a combinatorial region, where at least 90% of the combinatorial regions in the phage display library include at least one in-frame amber codon, and where the at least one in-frame amber codon is within an encoding region of a peptide that binds to the ligand binding site of the desired target; (b) transforming the phage display library into bacterial host cells, where the bacterial host cells are capable of translating the combinatorial region of the phage coat protein gene such that the at least one in-frame amber codon encodes a desired non-canonical amino acid, where the bacterial host cells are co-infected with a knockout helper phage that does not express the phage coat protein gene, and where the transforming allows for the production of phage particles that contain the phage coat protein with the desired non-canonical amino acid in the combinatorial region; (c) screening the phage particles against the desired target, where the screening results in the selection of phage particles with phage coat protein combinatorial regions that bind to the ligand binding site of the desired target, and where the non-canonical amino acid acts as a ligand to direct the phage coat protein combinatorial region to the ligand binding site of the desired target; and (d) identifying the amino acid sequences of the combinatorial regions of the selected phage particles.

Additional embodiments of the present disclosure pertain to peptides that have been screened from the phage display libraries and methods of the present disclosure. For instance, in some embodiments, the present disclosure pertains to compositions that include an inhibitor of sirtuin 2. In some embodiments, the present disclosure pertains to compositions that include an inhibitor of ENL.

DESCRIPTION OF THE DRAWINGS

FIG. 3 illustrates the results of superinfection-selection.

FIG. 4 illustrates the genetic incorporation of non-canonical amino acids (ncAAs) into a phage-displayed peptide library.

FIG. 5 illustrates the amino acid sequence of selected peptides containing ncAAs. FIG. 5A shows the amino acid sequence of peptides isolated after the third and fourth round of selection against streptavidin. FIG. 5B shows the amino acid sequence of peptides isolated after the third round of selection against SIRT2. The X represents the position of the ncAAs mBrF or BuK as determined by the position of the amber codon in the DNA sequence.

FIG. 6 illustrates molecular dynamics simulations and inhibition of human sirtuins (SIRT) in vitro and in vivo. FIG. 6A shows a molecular dynamics simulation (frame 95/1000) of SIRT2 in complex with the peptide S2P03. Hydrophobic residues in SIRT2 that interact with the residues flanking thBuK in the peptide are shown in orange. FIG. 6B shows inhibition of human sirtuins 1-3 by S2P04 (left) and TB (right). Error bars represent one standard deviation of the mean of at least two independent experiments. FIG. 6C shows representative Western blots for a-tubulin acetylation and total a-tubulin in MCF-7 and HEK 293T cells treated with 50 µM S2P04, TB, or vehicle (0.25% DMF) for 24 hours.

FIG. 7 illustrates methods of selecting inhibitors of ENL.

FIG. 8 provides the structures and properties of various ENL inhibitors.

FIG. 9 summarizes inhibitory activities of selected peptides and TB. Values are given as the mean±standard deviation of two independent experiments.

DETAILED DESCRIPTION

Figure 1A:
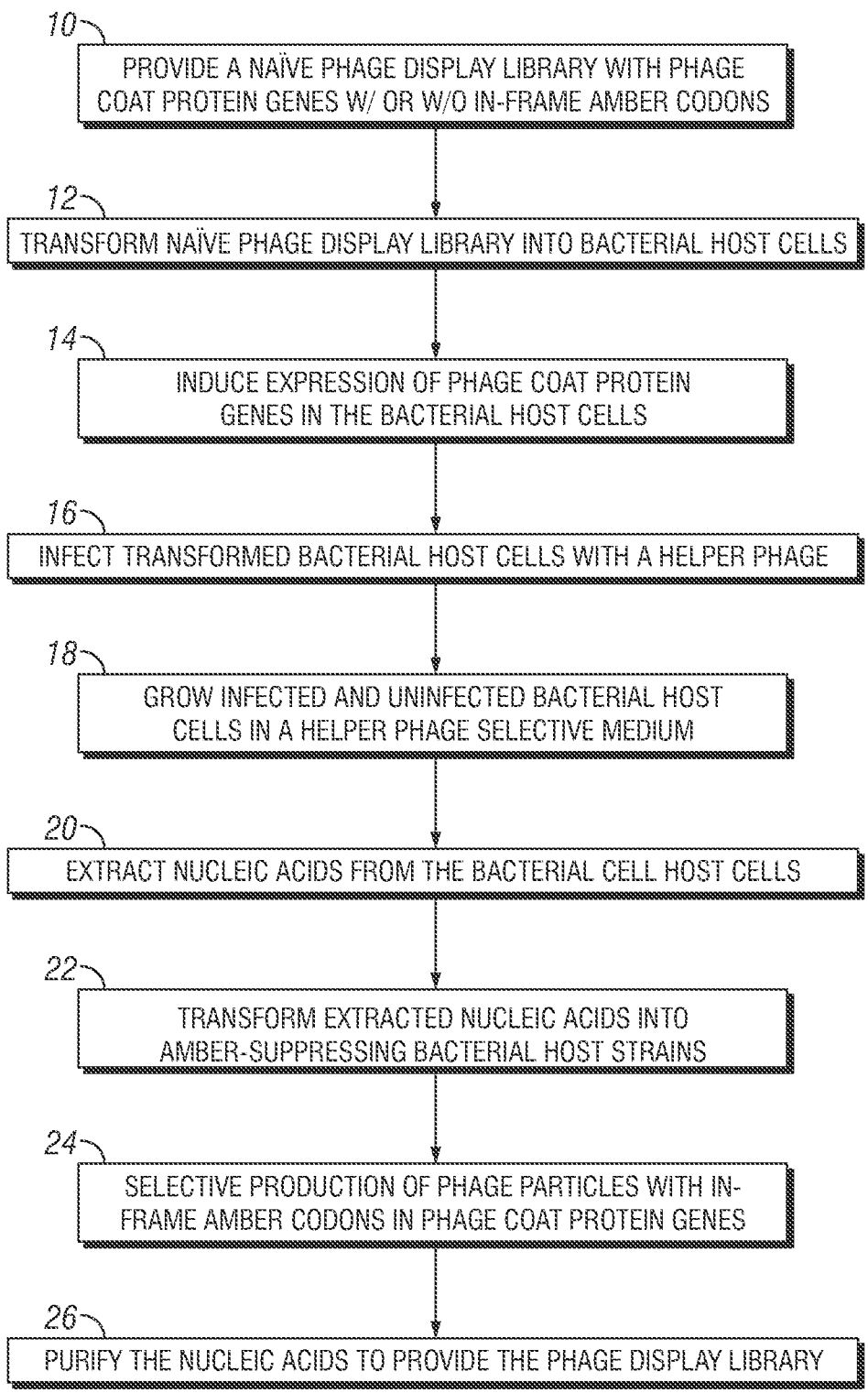
FIG. 1 provides schemes of methods of making a phage display library (FIG. 1A) and utilizing the phage display library to select noncanonical amino acid-containing peptides or proteins that bind to a target (FIG. 1B).
FIG. 1C illustrates an embodiment of active-site directed ligand evolution using phage display. Diagram A shows the binding of a target and a ligand to form a protein-ligand complex. The target is a biomacromolecule that is either a RNA or a protein. Diagram B illustrates a phage-assisted, active-site directed ligand evolution to identify high affinity ligands of a protein target. A ligand-containing non-canonical amino acid is incorporated into a phage-displayed, randomized peptide library for facilitating the binding to the protein target. Amino acid residues flanking the ligand-containing non-canonical amino acids provide additional interactions with the protein target for improved binding.
FIG. 1D shows the structures of various non-canonical amino acids.

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that include more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Phage display has several advantages over traditional random screening methods used in drug discovery. Such advantages include simplicity, cost effectiveness, and speed.

For instance, libraries can be screened rapidly for binding to a target and the 'selectants' eventually identified through DNA sequencing. Likewise, an enormously diverse exogenous library of peptides or proteins can be displayed on the surface of the phage using standard yet rapid molecular biology methods as opposed to using genetically engineered protein or peptide variants individually.

Peptide phage display employing large libraries accompanied by high throughput screening has played an important role in the development of clinically useful peptides and peptidomimetics. For instance, peptides are now used widely as therapeutic drugs and diagnostics in clinical applications such as endocrinology, oncology, urology, and obstetrics. Moreover, peptides often have numerous advantages over proteins, including antibodies, with respect to manufacturing costs, activity, stability, immunogenicity, and efficiency of organ penetration.

In fact, the current annual market of peptide drugs is $300-500 million with an annual growth rate of 25%. In addition, several peptide drugs developed using phage display have been approved for use in the clinic or are in clinical trials.

The first marketed peptibody, Nplate1 (Romiplostim, AMG 531), is an agonist of the thrombopoietin receptor used for the treatment of immune thrombocytopenic purpura. The peptide component of this peptibody has undergone substantial development, but owes its origin to a phage-displayed peptide library.

Finding high affinity peptides and proteins useful for diagnostic and therapeutic purposes can also be achieved by alternative display methods which have their roots in the original phage display concept. These methods can be broadly categorized into either cell-surface or cell-free display systems. However, cell-based methods are limited by the size of the library due to DNA transformation efficiency and any toxicity of the displayed molecules to the host cell.

Chemical modification strategies have also been employed to improve the pharmacokinetics of peptides. For instance, functional groups such as a phosphate esters have been added to the N-terminus of a peptide to improve binding by serum albumin or other serum proteins to extend half-life. However, no effective technology can combine phage display and chemical modification in generating peptide libraries. Furthermore, effective strategies do not exist for incorporating non-canonical amino acids in a cell-surface display.

The aforementioned limitations become more apparent in areas such as oncology, where potential ligand targets must bear epigenetic modifications in addition to the 20 natural amino acids. Various embodiments of the present disclosure address the aforementioned limitations.

In some embodiments, the present disclosure pertains to amber-obligated phage display libraries that can be utilized to effectively produce peptides or proteins that contain non-canonical amino acids. In some embodiments, the present disclosure pertains to methods of constructing the aforementioned amber-obligated phage display libraries. Additional embodiments of the present disclosure pertain to methods of selecting peptides or proteins that bind to a desired target by utilizing the phage display libraries of the present disclosure. Further embodiments of the present disclosure pertain to peptides that have been selected by utilizing the methods of the present disclosure, such as compositions that include one or more inhibitors of sirtuin 2 or ENL.

In some embodiments, the present disclosure pertains to a general strategy that incorporates a non-canonical amino acid that acts as a ligand (or is chemically modified to form a ligand) for a desired target into a phage display library. In some embodiments, the present disclosure pertains to the construction of a phage display library where an incorporated non-canonical amino acid directs phage displayed peptides to bind to the ligand binding site of a desired target and facilitate the selection of potent ligands that bind directly to the ligand binding site of the desired target.

Further embodiments of the present disclosure pertain to the incorporated non-canonical amino acids. In some embodiments, the incorporated non-canonical amino acids are the same as the post-translationally modified amino acids that directly interact with epigenetic enzymes and epigenetic reader proteins. In some embodiments, the incorporated non-canonical amino acids are the same as unnatural amino acids that bind to active sites of cellular proteins.

Amber-Obligated Phage Display Libraries

In some embodiments, the present disclosure pertains to a phage display library with a plurality of nucleic acids. The plurality of nucleic acids include nucleic acids with a phage coat protein gene that includes a combinatorial region. In some embodiments, at least 90% of the combinatorial regions in the phage display library include at least one in-frame amber codon.

Additional embodiments of the present disclosure pertain to methods of constructing the phage display libraries of the present disclosure. In some embodiments illustrated in FIG. 1A, the methods of the present disclosure include: (a) providing a naïve phage display library, where the naïve phage display library includes a plurality of nucleic acids with phage coat protein genes that include a combinatorial region, where the combinatorial regions of at least some of the nucleic acids include at least one in-frame amber codon (step 10); (b) transforming the naïve phage display library into bacterial host cells (step 12); (c) inducing expression of the phage coat protein gene in the transformed bacterial host cells, where the expression of phage coat proteins from nucleic acids that only contain in-frame sense codons in the phage coat protein genes renders the bacterial host cells immune to infection by a helper phage (step 14); (d) infecting the transformed bacterial host cells with the helper phage, where the helper phage encodes and expresses a gene that renders the infected bacteria resistant to an antibiotic (step 16); (e) growing the infected and uninfected bacterial host cells in a medium containing the antibiotic, where the growing results in the selection of the infected bacteria, and where the infected bacteria include the helper phage and at least some of the nucleic acids with phage coat protein genes that contain at least one in-frame amber codon in the combinatorial region (step 18); (f) extracting the nucleic acids from the bacterial cell host cells (step 20); (g) transforming the extracted nucleic acids into amber-suppressing bacterial host strains (step 22), where the amber-suppressing bacterial host strains are co-infected with a knockout helper phage that does not express the phage coat protein gene, and where the transforming allows for the selective production of phage particles from cells harboring nucleic acids that include phage coat protein genes with at least one in-frame amber codon in the combinatorial region (step 24); and (h) purifying the nucleic acids from the produced phage particles to provide the phage display libraries of the present disclosure (step 26).

The methods of the present disclosure can have numerous embodiments. For instance, in some embodiments, the naïve phage display library is prepared by site-directed mutagenesis.

In some embodiments, the phage display library includes a plurality of phages. In some embodiments, the plurality of nucleic acids in the phage display library include the nucleic acids of the phages.

In some embodiments, the phage display library includes a plurality of phagemids. In some embodiments, the nucleic acids in the phage display library include the nucleic acids of the phagemids.

In some embodiments, the phage coat protein gene is the PIII gene. In some embodiments, the bacterial host cells include *E. coli* bearing an F sex pilus.

In some embodiments, the phage coat protein gene is positioned near an IPTG-inducible promoter. In some of such embodiments, the phage coat protein is expressed by exposing the bacterial host cells to IPTG.

In some embodiments, the helper phage is a CM13 helper phage. In some embodiments, the helper phage encodes and expresses a gene that renders the infected bacteria resistant to kanamycin. As such, in some embodiments, selective growth occurs in a medium containing kanamycin.

The phage display libraries of the present disclosure can also have numerous embodiments. For instance, in some embodiments, more than 90% of the combinatorial regions in the phage display library include at least one in-frame amber codon. In some embodiments, more than 95% of the combinatorial regions in the phage display library include at least one in-frame amber codon. In some embodiments, more than 99% of the combinatorial regions in the phage display library include at least one in-frame amber codon.

In some embodiments, the combinatorial region in at least some of the nucleic acids in the phage display library include a plurality of in-frame amber codons. In some embodiments, the plurality of in-frame amber codons are randomly distributed throughout the combinatorial region. In some embodiments, the at least one in-frame amber codon is within a region of a peptide that binds to a ligand binding site of a protein.

In some embodiments, the combinatorial region encodes a peptide. In some embodiments, the combinatorial region encodes a protein.

Methods of Selecting Peptides or Proteins that Bind to a Desired Target

Figure 1B:
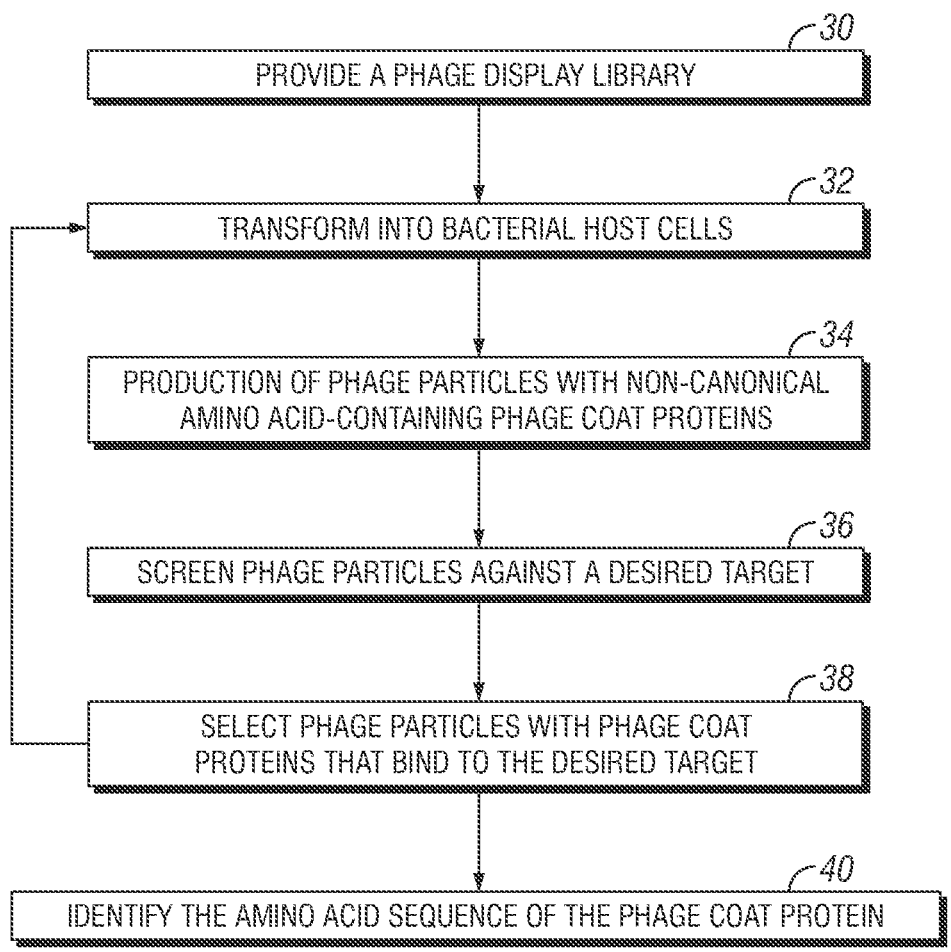
Figure 1C:
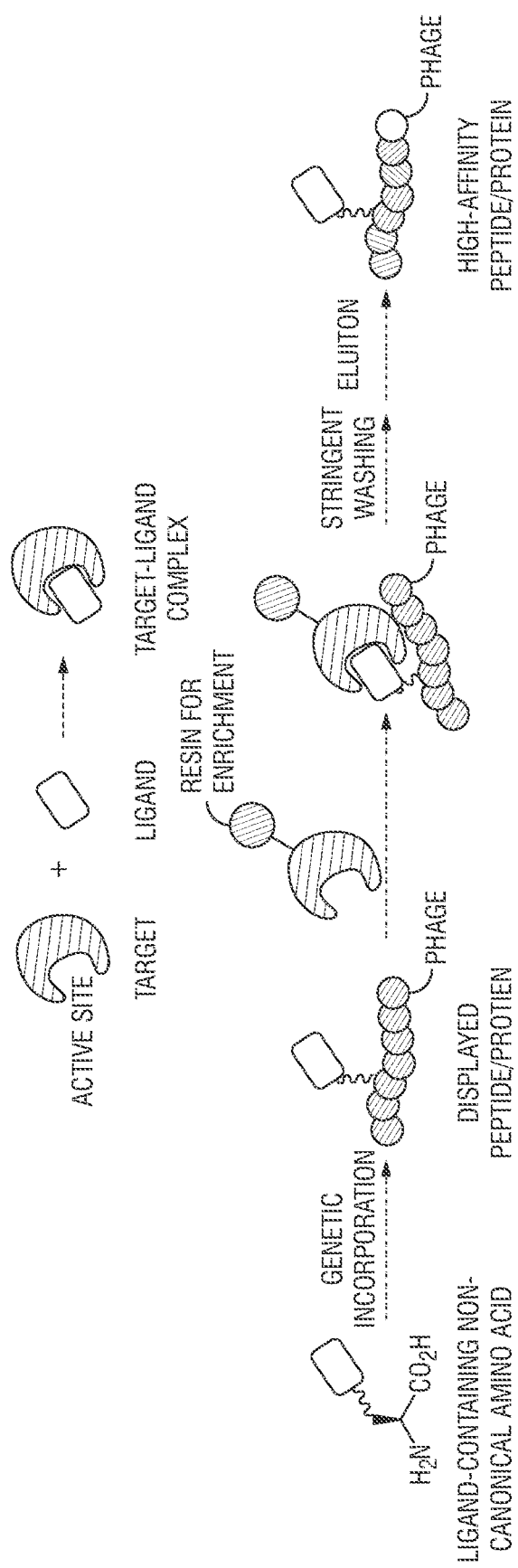

Additional embodiments of the present disclosure pertain to methods of selecting peptides or proteins that bind to a desired target by utilizing the phage display libraries of the present disclosure. In some embodiments illustrated in FIG. 1B, the methods of the present disclosure include: (a) providing a phage display library of the present disclosure (step 30); (b) transforming the phage display library into bacterial host cells (step 32), where the bacterial host cells are capable of translating the combinatorial region of the phage coat protein gene such that the in-frame amber codons in the combinatorial region encode a desired non-canonical amino acid, where the bacterial host cells are co-infected with a knockout helper phage that does not express the phage coat protein gene, and where the transforming allows for the production of phage particles that contain the phage coat protein with the desired non-canonical amino acid in the combinatorial region (step 34); (c) screening the phage particles against the desired target (step 36), where the screening results in the selection of phage particles with phage coat protein combinatorial regions that bind to the desired target (step 38); and (d) identifying the amino acid sequences of the combinatorial regions of the selected phage particles in order to identify the selected peptides or proteins (step 40).

In more specific embodiments, the present disclosure pertains to methods of selecting peptides that bind to a ligand binding site of a desired target through the following steps: (a) providing a phage display library comprising a plurality of nucleic acids, where the plurality of nucleic acids include nucleic acids with a phage coat protein gene that includes a combinatorial region, where at least 90% of the combinatorial regions in the phage display library include at least one in-frame amber codon, and where the at least one in-frame amber codon is within an encoding region of a peptide that binds to the ligand binding site of the desired target; (b) transforming the phage display library into bacterial host cells, where the bacterial host cells are capable of translating the combinatorial region of the phage coat protein gene such that the at least one in-frame amber codon encodes a desired non-canonical amino acid, where the bacterial host cells are co-infected with a knockout helper phage that does not express the phage coat protein gene, and where the transforming allows for the production of phage particles that contain the phage coat protein with the desired non-canonical amino acid in the combinatorial region; (c) screening the phage particles against the desired target, where the screening results in the selection of phage particles with phage coat protein combinatorial regions that bind to the ligand binding site of the desired target, and where the non-canonical amino acid acts as a ligand to direct the phage coat protein combinatorial region to the ligand binding site of the desired target; and (d) identifying the amino acid sequences of the combinatorial regions of the selected phage particles.

The selection methods of the present disclosure can also have numerous embodiments. For instance, in some embodiments, the screening step occurs by affinity selection against a desired target. In some embodiments, the screening step occurs by: (1) incubating the phage particles with a desired target that is immobilized on a surface; (2) separating unbound phage particles from phage particles that are bound to the desired target; and (3) isolating the bound phage particles. In some embodiments, the separation step may occur by washing away unbound phage particles from phage particles that are bound to the desired target.

In some embodiments, the desired target may be biotinylated and immobilized on a streptavidin surface. In some of such embodiments, screening may occur by (1) incubating the phage particles with the desired target that is immobilized on the streptavidin surface; (2) separating unbound phage particles from phage particles that are bound to the desired target by a washing step; and (3) isolating the bound phage particles by competitively eluting the bound phage particles with biotin, or by adding an acidic buffer (e.g., at pH 2) to release the bound phage particles.

In some embodiments, the screening may occur multiple times. For instance, in some embodiments, the screening step further comprises: (1) transforming the selected phage particles into the bacterial host cells to allow for the production of additional phage particles; and (2) re-screening the phage particles in accordance with step (c) (outlined above and illustrated as step 36 in FIG. 1B). In some embodiments, the further screening may be repeated multiple times.

In some embodiments, the screening results in the selection of phage particles with phage coat protein combinatorial regions that bind to a ligand binding site of a desired target. In some embodiments, the non-canonical amino acid acts as a ligand to direct the phage coat combinatorial region to the ligand binding site of the desired target. In some embodiments, the ligand inhibits the activity of one or more epigenetic enzymes or epigenetic reader proteins.

Various methods may also be utilized to identify the amino acid sequences of the combinatorial regions of the selected phage particles. For instance, in some embodiments, the identifying occurs by sequencing the combinatorial regions of the selected phage particles. In some embodiments, the identification occurs by: (1) purifying the selected phage particles; (2) isolating the nucleic acids from the selected phage particles; and (3) sequencing the combinatorial regions of the nucleic acids.

The methods of the present disclosure may also utilize various bacterial host cells. For instance, in some embodiments, the bacterial host cell is an amber-suppressing bacterial host strain. In some embodiments, the bacterial host cell contains an amber suppressor tRNA that has been aminoacylated with the desired non-canonical amino acid by a cognate aminoacyl-tRNA synthetase. In some embodiments, the desired non-canonical amino acids are incorporated during translation in response to in-frame amber codons by the amber suppressor tRNA.

In more specific embodiments, the bacterial host cell is a bacteria that has been transformed with three plasmids: (1) a plasmid that encodes a phage coat protein gene with at least one in-frame amber codon in a combinatorial region; 2) a plasmid that encodes an amber suppressor tRNA and a cognate aminoacyl-tRNA synthetase that can link a desired non-canonical amino acid to the suppressor tRNA; and (3) a helper phage that encodes all the essential phage proteins except the phage coat protein containing the combinatorial region.

Figure 1D:
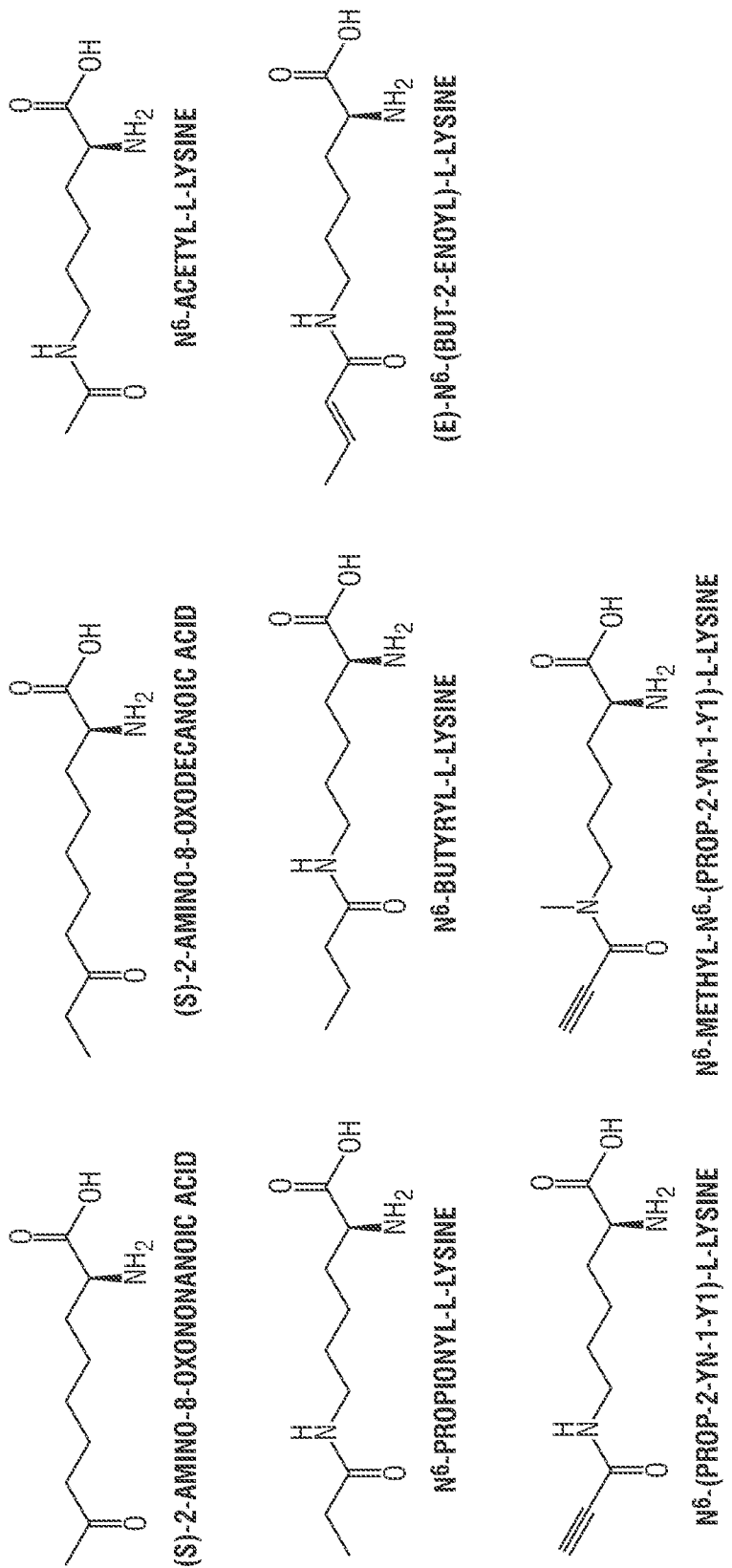

The methods of the present disclosure can be utilized to incorporate various non-canonical amino acids into the combinatorial regions of phage coat proteins. For instance, in some embodiments, the desired non-canonical amino acids include, without limitation, phenylalanine-derived non-canonical amino acids, lysine-derived non-canonical amino acids, and combinations thereof. In some embodiments, the desired non-canonical amino acids include, without limitation, S-2-amino-8-oxononanoic acid, S-amino-8-oxodecanoic acid, $N^6$-acetyl-L-lysine, $N^6$-propionyl-L-lysine, $N^6$-butyryl-L-lysine, $N^6$-crotonyl-L-lysine, $N^6$-(prop-2-yn-1-yl)-lysine, $N^6$-methyl-$N^6$-$N^6$-(prop-2-yn-1-yl)-lysine, and combinations thereof. The structures of the aforementioned non-canonical amino acids are shown in FIG. 1D.

The methods of the present disclosure may be utilized to screen peptides or proteins in combinatorial regions of phage coat proteins against various desired targets. For instance, in some embodiments, the desired targets include, without limitation, peptides, proteins, enzymes, small molecules, cell receptors, antigens, ligand binding sites of a protein, active sites of a desired target, active sites of a protein, and combinations thereof. In some embodiments, the desired target is a ligand binding site of a protein. In some embodiments, the ligand binding site is the active site of a protein. In some embodiments, the ligand binding site is an allosteric site of a desired protein. In some embodiments, the desired target is an enzyme, such as sirtuin 2.

Inhibitors of Sirtuin 2

Additional embodiments of the present disclosure pertain to peptide inhibitors of sirtuin 2 that have been selected by utilizing the methods of the present disclosure. More specific embodiments of the present disclosure pertain to compositions that include an inhibitor of sirtuin 2. In some embodiments, the inhibitor of sirtuin 2 includes, without limitation: (a) CTVXTSL (SEQ ID NO:1); (b) TCTVXIG (SEQ ID NO:2); (c) CTFXVPT (SEQ ID NO:3); (d) CTVXI (SEQ ID NO:4); (e) ZTVXI (SEQ ID NO:5); or (f) combinations thereof. In some embodiments, X is a non-canonical amino acid. In some embodiments, Z is a non-canonical amino acid or aminobutyric acid.

In some embodiments, the inhibitor of sirtuin 2 is $NH_2$-CTVXTSL-$NH_2$ (S2P03). In some embodiments, the inhibitor of sirtuin 2 is $NH_2$-TCTVXIG-$NH_2$ (S2P04). In some embodiments, the inhibitor of sirtuin 2 is $NH_2$-CTFXVPT-$NH_2$ (S2P07). In some embodiments, the inhibitor of sirtuin 2 is Ac-CTVXI-$NH_2$ (Ac-S2P04-5). In some embodiments, the inhibitor of sirtuin 2 is $NH_2$-ZTVXI-$NH_2$, where Z is aminobutyric acid (S2P04 (Abu)-5).

Inhibitors of SNL

Further embodiments of the present disclosure pertain to peptide inhibitors of SNL that have been selected by utilizing the methods of the present disclosure. More specific embodiments of the present disclosure pertain to compositions that include an inhibitor of SNL. In some embodiments, the inhibitor of SNL includes, without limitation: (a) DIWCFXG (SEQ ID NO: 6); (b) SXDIWCF (SEQ ID NO:7); or (c) combinations thereof. In some embodiments, X is a non-canonical amino acid.

In some embodiments, the inhibitor of SNL is DIWCFXG (SEQ ID NO: 6). In some embodiments, the inhibitor of SNL is SXDIWCF (SEQ ID NO:7).

Applications and Advantages

The methods and phage display libraries of the present disclosure can have various advantages and applications. For instance, in some embodiments, the methods of the present disclosure allow for highly efficient non-canonical amino acid incorporation into displayed peptides in order to expand the structural and functional diversity of phage display libraries. Moreover, the methods of the present disclosure can be used to generate libraries that are amenable to iterative rounds of selection and amplification that are required for directed evolution, thus allowing rapid identification of novel peptide ligands and monoclonal antibodies from enormous polypeptide libraries carrying functional groups not limited to those found in the 20 canonical amino acids.

In more specific embodiments, the phage display libraries and selection methods of the present disclosure can be utilized for ligand binding site-directed ligand evolution to identify inhibitors containing non-canonical amino acids with activity both in vitro and in vivo. In some embodiments, the inhibitors can include inhibitors of both Zinc- and NAD-dependent HDACs that bind to active site regions of enzymes with high specificity.

In some embodiments, the phage display libraries and selection methods of the present disclosure can be used to generate peptide libraries to screen and discover lead molecules in epigenetic regulation with increased drug potency.

Reference will now be made to more specific embodiments of the present disclosure and experimental results that provide support for such embodiments. However, Applicant notes that the disclosure below is for illustrative purposes only and is not intended to limit the scope of the claimed subject matter in any way.

Example 1. An Amber-Codon-Obligate Phage Display System Accompanying Active Site-Directed Ligand Evolution to Assist Drug Discovery Phage display technology enables the rapid identification of novel peptide ligands and monoclonal antibodies from enormous polypeptide libraries. However, these libraries are limited to the twenty canonical amino acids. Using orthogonal aminoacyl-tRNA synthetases and tRNAs, this repertoire can be expanded to include non-canonical amino acids (ncAAs). However, inefficient ncAA incorporation biases phage libraries and has limited the widespread adoption of this technique.

In this Example, Applicant reports a method, termed superinfection-selection, for constructing phage display libraries in which every clone contains an ncAA encoded by an in-frame amber codon. Such amber-codon-obligate libraries abrogate bias from inefficient ncAA incorporation into displayed peptides. Applicant demonstrates that these libraries are amenable to iterative rounds of selection and amplification that are required for directed evolution. Using this technique, Applicant generated a library of peptides containing a genetically-encoded lysine posttranslational modification and used this library for active site-directed ligand evolution of peptides that inhibit sirtuin 2 both in vitro and in human cancer cells.

Phage display is a widely used tool for the selection of peptide ligands and monoclonal antibodies from large, combinatorial polypeptide libraries. In this technique, a DNA library is cloned as a genetic fusion to a gene encoding a phage coat protein. When the fusion protein is expressed and integrated into the viral capsid, the peptide library is 'displayed' on the surface of the virus. This configuration creates a physical link between the displayed peptide and its encoding DNA allowing for amplification of the library in a bacterial host and facile peptide sequence determination following rounds of target-directed selection. Phage-displayed libraries have been used for numerous applications ranging from epitope mapping to the identification of inhibitors of enzymes and protein-protein interactions and a number of phage-derived peptides and antibodies have been approved for pharmaceutical use or are in late-stage clinical trials. However, given that phage display libraries are expressed in *E. coli*, peptides within these libraries are confined to the 20 canonical amino acids, considerably limiting the sequence space that they can be used to explore.

Using orthogonal aminoacyl-tRNA synthetase (aaRS) and tRNA pairs, researchers have been able to artificially expand the genetic code to incorporate numerous non-canonical amino acids (ncAAs), bearing diverse functionalities, across a range of host organisms. In this technique, ncAAs are incorporated during translation in response to a redefined nonsense codon by an orthogonal suppressor tRNA that has been selectively aminoacylated with the ncAA by its cognate aaRS. Applying nonsense suppression to phage display, prior studies have demonstrated the genetic incorporation of several ncAAs into proteins and peptides displayed on the surface of bacteriophages. However, the selection of polypeptides containing ncAAs has proven extremely challenging, largely due to propagation bias against phage clones that contain an ncAA. This bias is the result of inefficient stop codon suppression which limits the production of the peptide-coat fusion protein and, thereby, lowers the reproductive rate of clones containing an ncAA with respect to those that contain only canonical amino acids. Although peptides and proteins containing ncAAs have been selected from these types of libraries, the requirements of highly efficient aaRS-tRNA pairs and extensive optimization of expression conditions has prohibited the widespread adoption of this technique.

To overcome the challenge of expression bias, Applicant has developed a general method for constructing phage display libraries in which every clone contains an ncAA that is encoded by an in-frame amber codon. Applicant demonstrates in this Example that such 'amber-codon-obligate' libraries are amenable to the display of peptides containing a variety of ncAAs, thereby greatly expanding the utility of phage display. Applicant validates the method for library construction by generating an amber-codon-obligate heptapeptide library displayed on the N-terminus of the minor coat protein (pIII) of the M13 bacteriophage. Applicant further demonstrates that this type of library is amenable to iterative rounds of amplification and selection with both phenylalanine- and lysine-derived ncAAs incorporated. Finally, Applicant uses the library containing a genetically encoded lysine posttranslational modification to select for peptides that bind to the active site of the lysine deacylase sirtuin 2. Applicant demonstrates that derivatives of these peptides are potent inhibitors of sirtuin 2-catalyzed lysine deacetylation in vitro and in vivo.

Example 1.1. Construction of an Amber-Codon-Obligate Phage Display Library

Phage display libraries capable of displaying peptides that contain ncAAs have been constructed via site-saturation mutagenesis using degenerate primers that cover 32 codons (including one amber codon) and encode all 20 canonical amino acids. Previous methods for constructing amber-codon-obligate libraries utilized primer pairs in which the position of the amber codon, and thus the ncAA, was fixed and all other positions were randomized. Applicant sought to construct a more diverse library in which the position of the amber codon could be randomly distributed throughout the peptide sequence. To construct such a library, one could, theoretically, use a combination of primer pairs in which the position of the amber codon is altered to cover each position within the sequence. Aside from the possibility of biasing the library through unequal mixing of the cloned products, this primer combination approach does not resolve a common problem associated with primer-based DNA library construction. Though they occur with low frequency, synthetic errors, such as nucleotide deletions, are unavoidable in oligonucleotide primers.

It is therefore inevitable to introduce clones without an amber codon into the library when using this approach. These clones, which do not rely on stop codon suppression, will have a significant growth advantage over amber-coding clones. During phage production, this propagation bias will cause these clones to be enriched and gradually mask amber-coding clones. Applicant have observed this problem in a parallel study that involved fixing one amber coding site.

Given the lack of alternative methods to resolve this problem, Applicant developed a general method for constructing amber-codon-obligate phage libraries that allows for random distribution of the ncAA. This method exploits a phenomenon of filamentous (Ff) phage biology known as superinfection immunity. Briefly, superinfection immunity describes the resistance of an infected bacterium to further infection (superinfection) by the same type of phage. For *E. coli* infected with Ff phages, superinfection immunity is granted by the phage coat protein pIII which is expressed in the host from the resident phage. Endogenously expressed pIII binds to TolA, an *E. coli* cell surface protein that is used by Ff phages as a receptor for host adsorption. The binding of endogenous pIII to TolA blocks adsorption, and therefore superinfection, by competing phages.

Applicant's strategy for constructing an amber-codon-obligate phage display library involved two steps. In the first step, Applicant constructed a naïve library as a genetic fusion to the phage coat protein pIII. The library was constructed using degenerate primers and, therefore, contained sequences with amber codons and those with only sense codons. In a second step, dubbed "superinfection-selection", Applicant exploited the principle of superinfection immunity to select for library members containing amber codons, removing those that contain only sense codons from the library pool.

Applicant began by constructing a naïve, combinatorial heptapeptide library fused to pIII. To clone the library, Applicant introduced seven randomized (NNK) codons via site-saturation mutagenesis as a genetic fusion to the N-terminus of pIII on the pADL-10b phagemid. Following cloning, Applicant used the purified library to transform electrocompetent E. coli Top10 F' yielding $1.4 \times 10^9$ unique transformants (theoretical peptide diversity=$1.8 \times 10^9$).

Figure 2:
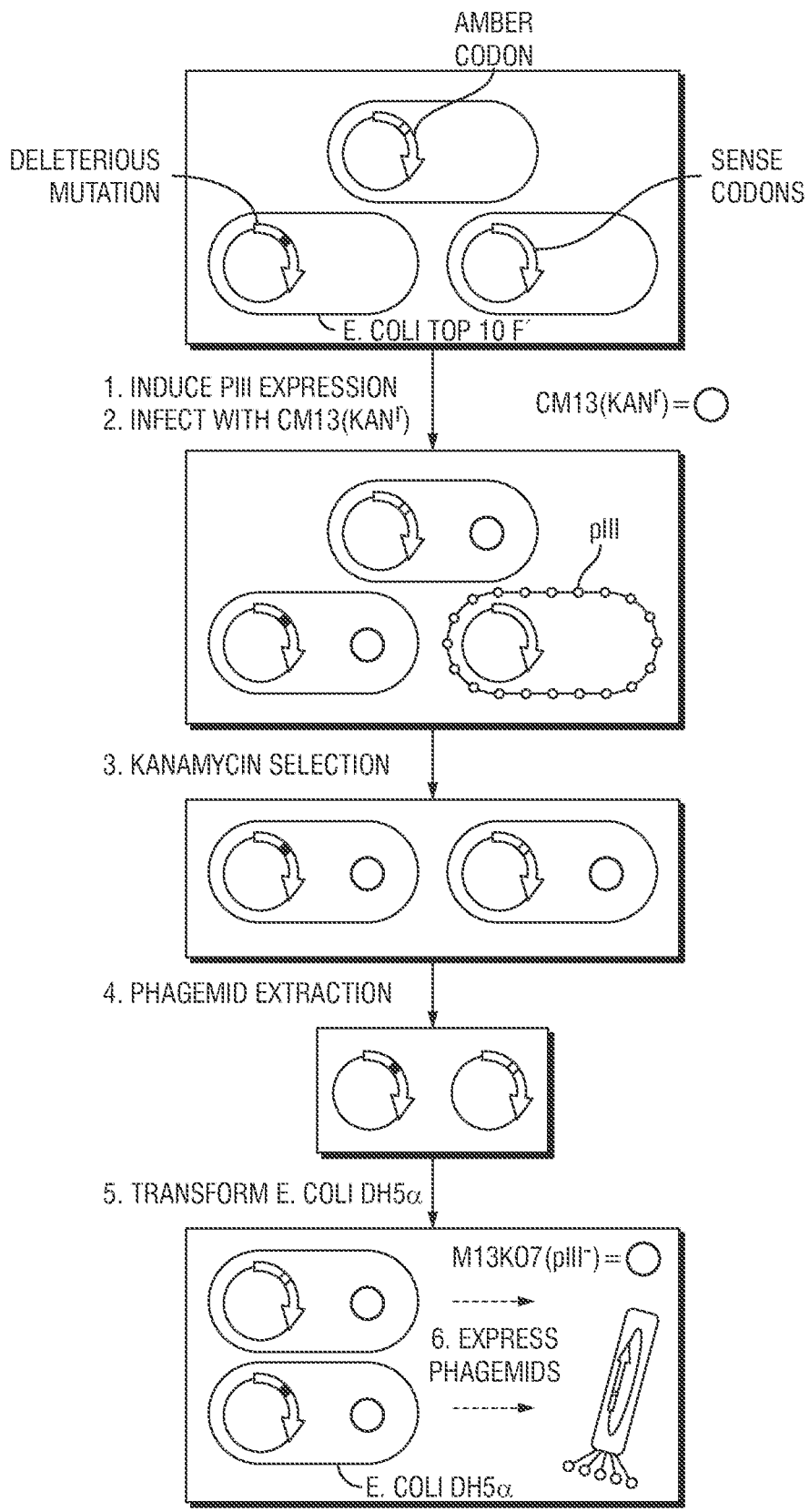
FIG. 2 is a schematic representation of a method for constructing amber-codon-obligate phage display libraries by superinfection-selection. Following cloning, the naïve phagemid library is used to transform $E.\ coli$ bearing an F sex pilus (FIGS. 2A-B). The expression of pIII is induced with IPTG and shortly after, cells are superinfected with the CM13 helper phage (FIG. 2A). The expression of pIII in cells harboring a copy of the library that contains only sense codons renders these cells immune to superinfection (FIG. 2B). Changing the media to one containing kanamycin allows for the selective growth of cells harboring a copy of the library that contains in-frame amber codons (FIG. 2C). Cells harboring a copy of the library with deleterious mutations also pass this selection. The phagemid library is purified (FIG. 2D) and used to transform DH5a, an amber-suppressing strain of $E.\ coli$ (FIG. 2E). Complementation of the phagemid with a pIII-knockout helper phage in $E.\ coli$ DH5a allows for the production of phagemid particles only from cells harboring a copy of the peptide-pIII library containing in-frame amber codons.

Next, Applicant carried out superinfection-selection to select for library clones that contained in-frame amber codons. Applicant grew E. coli Top10 F' harboring the phagemid library in media supplemented with ampicillin and tetracycline to early log-phase, at which point Applicant induced the expression of pIII with the addition of IPTG (FIG. 2A). Under these conditions, full-length pIII is expressed in cells that harbor a copy of the library with only sense codons. However, translation termination prevents the expression of pIII in cells harboring a copy of the library containing amber codons (FIG. 2B).

Since superinfection immunity is granted by endogenous pIII, the former are immune to superinfection and the latter are vulnerable to superinfection. After inducing the expression of pIII, Applicant infected the culture with the CM13 helper phage, which bears a gene conferring kanamycin resistance. Following superinfection with CM13, Applicant changed the media to one containing 25 μg·mL$^{-1}$ kanamycin, which allowed for the selective growth of cells that were susceptible to superinfection (i.e., those harboring a copy of the library that contained an in-frame amber codon) (FIG. 2C).

Applicant sequenced several of the library clones after one round of superinfection-selection. The sequences revealed that, along with clones that contain amber codons, a number of clones that contain deleterious mutations in the peptide or pIII coding region were also enriched. These mutations prevented the expression of functional pIII and thus allowed the clone to pass through the selection.

To cure the population of these unwanted clones, Applicant purified the phagemid library and used the purified library to transform E. coli DH5α. DH5α is a supE strain of E. coli that incorporates glutamine in response to amber codons. Therefore, expressing the library in this strain allows for the production of full-length pIII in clones that contain amber codons, but not in those that contain deleterious mutations.

Applicant complemented the phagemid library with M13KO7(pIII$^-$), a helper phage that contains a nonsense (TAA) mutation in gene III and is therefore unable to produce its own pIII. Complementation with M13KO7 (pIII$^-$) resulted in the selective expression of phagemid particles from clones that contained amber codons within the peptide sequence (FIGS. 2D-E). To confirm the successful removal of deleterious clones, Applicant sequenced several of the phagemids after expression. None of the clones expressed in DH5α that Applicant sequenced contained deleterious mutations that would prevent pIII expression. Following passage through DH5a, Applicant purified the phagemid particles and used them to infect E. coli Top10 F' for an additional round of superinfection-selection.

Over the two rounds of superinfection-selection, Applicant monitored amber codon enrichment by measuring the percentage of the population of E. coli that was susceptible to superinfection. In the first round, 18% of the population was susceptible to superinfection by the CM13 helper phage. This is consistent with theoretical calculations which predict 19.9% of the clones to contain at least one amber codon in a library of seven NNK codons, based on a binomial distribution, using a probability of $\frac{1}{32}$ for amber codons. After the second round of selection, greater than 98% of the population was susceptible to superinfection, suggesting a large increase in the number of clones that contained amber codons between rounds 1 and 2 (FIG. 3A).

Figures 3A, 3B:
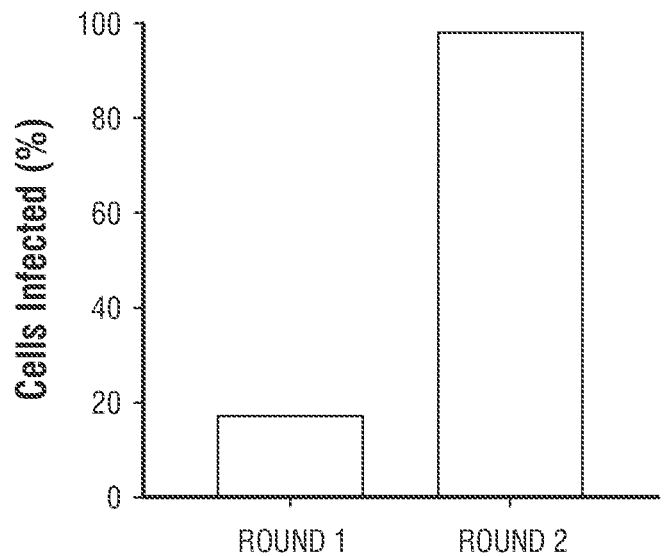
FIG. 3A shows that, during both rounds of superinfection-selection, the percentage of the population that was susceptible to superinfection (e.g., clones that contained amber codons) was monitored by growth on kanamycin. The increase in the number of cells that were susceptible to superinfection between rounds 1 and 2 is indicative of the successful selection of library clones containing amber codons.
FIG. 3B shows sequencing analysis after the second round of superinfection-selection confirmed the presence of an in-frame amber codon in every clone.

Sequencing of the library after the second round of superinfection-selection confirmed the successful selection as all of the clones that Applicant sequenced (n=10) contained an amber codon within the random sequence (FIG. 3B). These data demonstrate that superinfection-selection is a valid strategy for generating amber-codon-obligate phage display libraries.

Example 1.2. Genetic Incorporation of ncAAs into Phage-Displayed Peptides

Figure 4A:
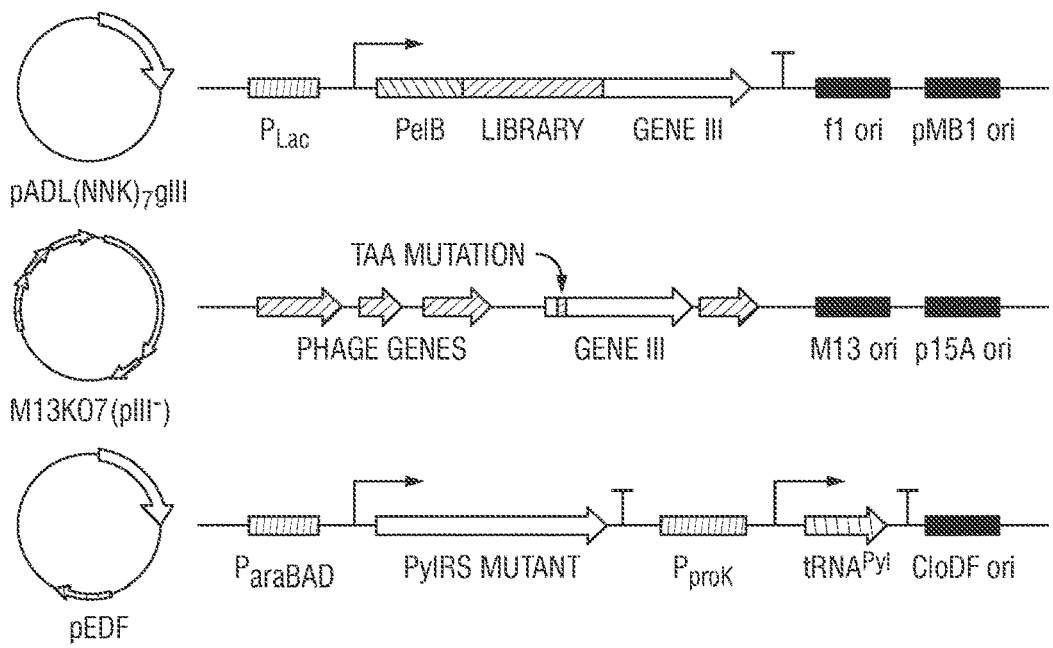
FIG. 4A provides a schematic representation of the three-plasmid system used to incorporate ncAAs into the peptide library.
Figure 4B:
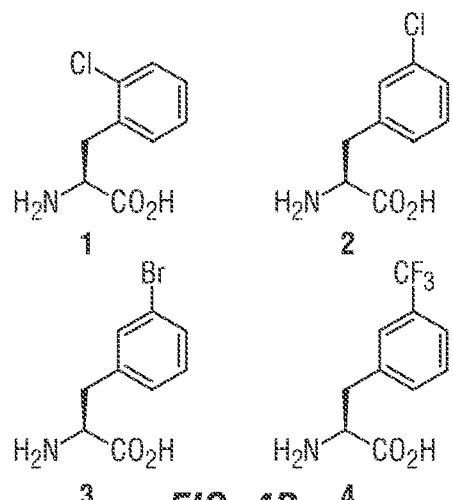
FIG. 4B shows the structures of phenylalanine derivatives 1-4.
Figure 4C:
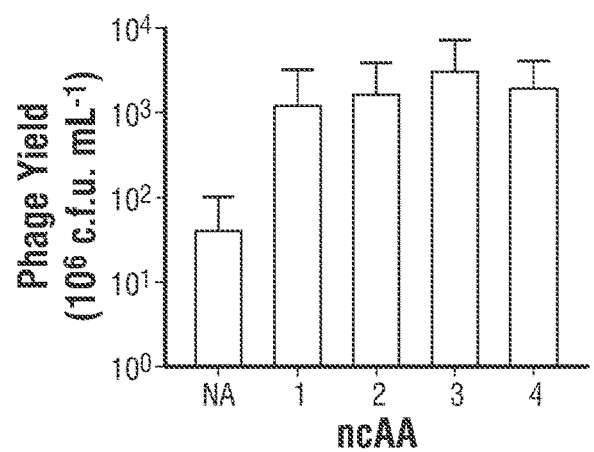
FIG. 4C shows phage yield in the presence and absence (NA) of 4 mM of ncAAs 1-4. The yield is displayed in millions of colony forming units per milliliter of culture media. Error bars represent one standard deviation of the mean of at least three independent experiments.

Applicant tested the genetic incorporation of phenylalanine and lysine derivatives into the amber-codon-obligate library using derivatives of the pyrrolysyl-tRNA synthetase (PylRS) in conjunction with its cognate, amber-suppressing tRNA (tRNA$_{CUA}^{Pyl}$). Applicant first tested the incorporation of phenylalanine derivatives containing substitutions at the ortho and meta positions of the phenyl ring. To incorporate these ncAAs into the peptide library, Applicant utilized a previously reported PylRS mutant that contains alanine mutations at positions N346 and C348 (PhdRS). To express the phagemid particles, Applicant transformed E. coli Top10 with three plasmids: 1) pADL(NNK)$_7$gIII, which encodes the amber-codon-obligate peptide-pIII library, 2) pEDF-PhdRS, which contains the genes encoding PhdRS and tRNA$_{CUA}^{Pyl}$, and 3) M13KO7(pIII$^-$), which encodes all essential phage proteins except pIII (FIG. 4A). Applicant grew the transformed cells in 2×YT media supplemented with 4 mM of one of the four phenylalanine derivatives 1-4 (FIG. 4B), which resulted in a 36 to 83-fold increase in phagemid particle yield compared to when no ncAA was added to the growth media (FIG. 4C).

The ncAA-dependent increase in particle yield is consistent with suppression of the amber codon by tRNA$_{CUA}^{Pyk}$ and indicates the successful incorporation of the ncAAs into the phage-displayed peptide library. The low level of background phagemid production in the absence of an ncAA is likely due to phenylalanine incorporation as Applicant has shown that mis-aminoacylation of tRNA$_{CUA}^{Pyl}$ with phenylalanine is a common observation among evolved PylRSs, albeit to a small degree.

Figure 4D:
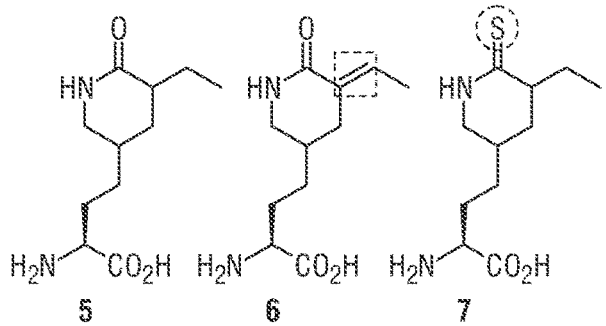
FIG. 4D shows the structures of lysine derivatives 5-7.

Following Applicant's success with incorporating phenylalanine derivatives, Applicant next tested the incorporation of lysine derivatives into the peptide library. Applicant chose two lysine derivatives to test their incorporation: Ne-butyryl-lysine (5, BuK) and N$^\varepsilon$-crotonyl-lysine (6, CrK) (FIG. 4D). Both of these ncAAs represent natural lysine posttranslational modifications. As such, peptide libraries containing these ncAAs could prove useful for studying the enzymes that natively interact with these modifications.

Figure 4E:
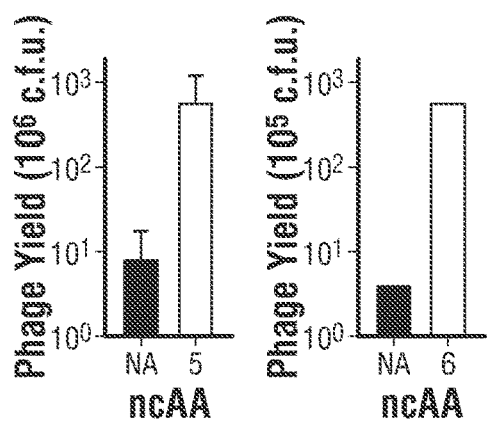
FIG. 4E shows a phage yield in the presence and absence (NA) of lysine derivatives 5 and 6. The yield is displayed in millions or hundred thousands of colony forming units for compounds 5 and 6, respectively. Error bars represent one standard deviation of the mean of three independent experiments.

To incorporate BuK and CrK, Applicant used a previously reported PylRS mutant containing a tryptophan mutation at position Y384 (BuKRS). Applicant has shown that BuKRS, in conjunction with tRNAP$_{CUA}^{Pyl}$, can facilitate the efficient incorporation of both Buk and CrK in response to amber codons in proteins in *E. coli*. Applicant expressed the phagemid library in *E. coli* Top10 containing pEDF-BuKRS and M13KO7(pIII⁻), which led to minimal particle production in the absence of an ncAA. Whereas, adding 5 mM of BuK or CrK to the growth media resulted in an increase in the particle yield of nearly 100-fold, demonstrating the successful incorporation of these ncAAs into the phage-displayed peptide library (FIG. 4E).

Example 1.3. Library Integrity is Maintained Over Rounds of Amplification

Phage display-based directed evolution experiments necessitate robust libraries that can endure iterative rounds of amplification and target-directed selection. If the super-infection-selection strategy for library construction was unsuccessful in removing all of the clones containing only sense codons, or if acquired mutations during amplification result in the loss of the amber codon, propagation bias in favor of these sequences would impede selection efforts.

To investigate the integrity of Applicant's amber-codon-obligate library in the face of iterative rounds of amplification and selection, Applicant performed a mock selection against streptavidin. Applicant incubated the phage-displayed heptapeptide library (~5×10¹⁰ c.f.u.) that had been expressed in the presence of ncAA 3 (mBrF) with the immobilized streptavidin target, removed unbound phagemid particles by washing, and competitively eluted specifically bound particles with 0.1 mM biotin. Following each selection round, Applicant amplified the eluted phagemid particles in *E. coli* Top10 containing pEDF-PhdRS and M13KO7(pIII⁻) for further rounds of selection.

In total, Applicant performed four rounds of amplification and selection. Phagemid clones were sequenced after the third (n=6) and fourth (n=12) rounds. Notably, even after four rounds of amplification, all of the clones that were sequenced contained mBrF within the peptide sequence as indicated by the presence of an in-frame amber codon (FIG. 5A). These data demonstrate that the method of superinfection-selection generates robust libraries that can withstand the iterative rounds of amplification that are required for directed evolution.

Example 1.4. Selection of Peptides Containing N$^\varepsilon$-Butyryl-Lysine for the Inhibition of Sirtuin 2

The sirtuins are a group of NAD⁺-dependent lysine deacylases that catalyze the conversion of NAD⁺ and N$^\varepsilon$-acyl-lysine to lysine and O-acyl-ADP ribose. In their capacity as modulators of the lysine acylation level of proteins, the sirtuins have been implicated as key regulators of various cellular processes ranging from gene transcription and DNA repair to metabolism and aging. As such, the sirtuins have emerged as promising targets for therapeutic intervention in human disease. Recently, inhibitors of sirtuin 2 (SIRT2), a sirtuin isoform primarily localized in the cytoplasm, have been shown to have pronounced anticancer activity in cell and animal models of human cancer. SIRT2 inhibitors also show promise in the treatment of age-related neurodegenerative disease. Therefore, there is currently great interest in the development of potent and selective SIRT2 inhibitors.

Applicant envisioned that a phage-displayed peptide library containing a genetically encoded acyl-lysine ncAA could be used for active site-directed ligand evolution to reveal peptide sequences that bind to the active site of SIRT2. To this end, Applicant used the amber-codon-obligate library to express a library of greater than 300 million peptides containing a BuK residue and selected for sequences within this library that bind to SIRT2.

Using an *E. coli* strain harboring pEDF-BuKRS and M13KO7(pIII⁻), Applicant expressed the amber-codon-obligate library and subjected the purified phagemid library to affinity selection against recombinant human SIRT2. To avoid the catalytic removal of the butyryl modification during selection, Applicant performed selections against apo SIRT2 in the absence of NAD⁺. Applicant isolated phagemid clones that were eluted after the third round of affinity selection and sequenced their DNA (n=20). The peptide sequences of clones isolated after the third round of selection against SIRT2 are shown in FIG. 5B.

Sequencing of the phagemids after affinity selection against SIRT2 revealed that the population had converged on consensus sequences primarily involving the residues immediately adjacent to the BuK residue. Consistent with two previous studies in which modified peptide libraries were screened against SIRT2, Applicant observed an enrichment of valine and leucine residues at the position immediately N-terminal to BuK (−1 position). Applicant also observed a strong enrichment of phenylalanine at this position. Immediately C-terminal to BuK (+1 position), Applicant observed a strong enrichment of amino acids with aliphatic sidechains with greater than 50% of the isolated clones having an isoleucine, valine, leucine, or alanine at this position.

Together, these findings suggest a substrate preference of SIRT2 for sequences with hydrophobic residues adjacent to the modified lysine. To gain insight into how the selected peptides might interact with the enzyme, Applicant performed molecular dynamics simulations of the peptides in complex with SIRT2. The simulations revealed hydrophobic interactions between the residues flanking the acyl-lysine residue and residues Phe235 and Leu239 of SIRT2 (FIG. 6A). This observation provides a possible explanation for why Applicant and others have observed a preference for hydrophobic residues at these positions within peptide substrates. Also consistent with previous findings, Applicant observed an enrichment of serine and threonine residues at the +3 position. Threonine at +3 has been shown to make hydrogen bonding interactions with Gln265 of SIRT2, providing a plausible explanation for this observation. Of all of the clones sequenced from Applicant's selection, 25% contained the consensus motif Cys-Thr-Val/Phe-BuK-Val/Ile.

Replacing the acyl-lysine amide moiety of sirtuin substrates with a slowly-hydrolyzing thioamide analog has proven to be an effective strategy for inhibiting the sirtuin enzymes. As such, Applicant chemically synthesized each of the selected peptides containing the Cys-Thr-Val/Phe-Buk-Val/Ile motif with N$^\varepsilon$-thiobutyryl-lysine (7, thBuK) (FIG. 6D) in the place of BuK and tested the synthetic peptides for inhibition of SIRT2. As a reference compound, Applicant utilized TB (FIG. 9), a recently reported, potent, SIRT2-selective inhibitor.

All three of the peptides Applicant tested inhibited SIRT2 significantly better (up to 45-fold) than TB with IC$_{50}$ values ranging from 68-101 nM (FIG. 9). Since the consensus motif found in Applicant's selection included only five of the seven residues in the library, Applicant also synthesized a truncated version of one of the peptides (S2P04-5) containing only the five residues of the consensus motif. S2P04-5 inhibited SIRT2 with an IC$_{50}$ of 136±29 nM, slightly higher than that of its parent peptide S2P04. This observation suggests that, although the identity of residues at positions distal to the BuK may not be critical, interactions such as backbone hydrogen bonding may still contribute to the enzyme-ligand binding.

Applicant tested S2P04 for selectivity for SIRT2 by measuring its inhibitory properties towards two other sirtuin enzymes that also recognize lysine butyrylation: SIRT1 and SIRT3. S2P04 inhibited SIRT2 2.7- and 152-fold more potently than SIRT1 and SIRT3, respectively (FIG. 6B). This selectivity is comparable to that measured for TB, however, for each enzyme S2P04 was at least 33-fold more potent than TB.

Finally, Applicant tested the ability of S2P04, a selected peptide with intermediate potency, to inhibit SIRT2 in human embryonic kidney (HEK 293T) and breast cancer cells (MCF-7). To test the inhibition of SIRT2, Applicant incubated cell cultures for 24 hours in media containing 50 µM of S2P04, TB, or a vehicle control. Following incubation with the inhibitor, Applicant measured the acetylation level of lysine 40 of a-tubulin, a known deacetylation substrate of SIRT2.

Applicant observed an increase in a-tubulin acetylation in both MCF-7 and HEK 293T cells treated with S2P04, though the effect was greatest for the MCF-7 cell line (FIG. 6C). MCF-7 cells treated with TB also displayed an increase in a-tubulin acetylation compared to the control. However, the effect was lower than that observed for S2P04. This observation is consistent with the lower potency of TB in vitro. No increase in a-tubulin acetylation was observed in HEK 293T cells treated with TB.

Following the observation that S2P04 inhibits SIRT2 in vivo, Applicant synthesized two shortened derivatives of the peptide: Ac-S2P04-5 and S2P04 (Abu)-5. The former contains an N-terminal acetylation which may aid in cell permeability and proteolytic stability, and the latter contains an aminobutyric acid (Abu) in place of cysteine which is more redox stable. Although both peptides inhibited SIRT2 in vitro (FIG. 9), neither led to a greater increase in acetylation level compared to S2P04 in vivo. These data demonstrate that phage display libraries constructed via the method of superinfection-selection can be used for active site-directed ligand evolution to identify inhibitors containing ncAAs with activity both in vitro and in vivo.

Example 1.5. Discussion

Applicant have developed a method for constructing phage-displayed peptide libraries in which every member contains an ncAA that is encoded in response to a randomly distributed amber codon. Though Applicant's focus in this example was on constructing libraries of short peptides, larger proteins, such as antibodies, are routinely displayed on the surface of filamentous phages. Since superinfection-selection relies on an inherent property of Ff phage biology, this method is not limited by library design or size. Therefore, superinfection-selection can theoretically be applied to generate libraries of much larger peptides and proteins within the general constraints of pIII display.

Applicant validated the method for library construction by generating an amber-codon-obligate heptapeptide library fused to the N-terminus of the pIII protein on the M13 bacteriophage. Applicant further demonstrated that the expression of phagemid particles from this library was dependent on the addition of an ncAA to the growth media. Previous studies involving genetic code expansion of phage libraries were limited to highly efficient aaRS/ncAA pairs to minimize expression bias against library clones that contained ncAAs. However, the amber-codon-obligate library abrogates this bias. Therefore, despite their varying incorporation efficiencies, each of the ncAAs that Applicant tested were readily incorporated into the phage-displayed peptides without optimization.

To date, over 150 ncAAs containing natural posttranslational modifications, bioorthogonal functional groups, spectroscopic probes, and other unique chemical and structural motifs have been genetically encoded via nonsense suppression. The method reported in this Example provides a means to readily generate peptide libraries containing these diverse ncAAs, for which numerous applications can be envisaged.

As a demonstration of the utility of this technique, Applicant generated a peptide library containing a naturally occurring posttranslational modification and used this library for active site-directed ligand evolution of peptides that bind to SIRT2. Sequencing of phagemid particles after three rounds of selection revealed peptide sequences that were in agreement with previous library screens against SIRT2, validating Applicant's results.

The selected peptides synthesized with thBuK in place of BuK were demonstrated to be potent inhibitors of SIRT2-catalyzed lysine deacetylation. Although the selected peptides retained isoform selectivity comparable to TB, their higher potency led to greater inhibition of SIRT2 in vivo. The similar sirtuin selectivity of S2P04 and TB is not surprising given that SIRT1 and SIRT2 share a high sequence homology around their active site and peptide binding cleft. BuK contains a chemical moiety that naturally directs the binding of a peptide to the SIRT2 active site. Such active site-directed ligand evolution could be extended to other genetically encoded ncAAs, such as methyl-lysines, for the identification of histone demethylase ligands. Although not reported in this Example, small molecule ligands identified through high-throughput screening could be covalently attached to an ncAA and displayed on phagemids allowing for the identification of organo-peptide ligands. In conclusion, Applicant believes that the amber-codon-obligate phage display technique in combination with active site-directed ligand evolution will find great applications in the field of drug discovery.

Example 1.6. Molecular Cloning

Phagemid Library Construction

The phagemid pADL-10b, which contains the gene encoding pIII, was purchased from Antibody Design Labs. To introduce a seven-site library at the N-terminus of pIII, the phagemid was PCR-amplified using the primers PADL-g3-P1: 5'-CATGCCATGGCC(NNK)$_7$GCGGCGAAAGCGG-3' (SEQ ID NO: 11) and pADL-g3-P2: 5'-CATGCCATGGCCGGCTGGGCCGC-3' (SEQ ID NO: 12). The PCR product was digested with NcoI, ligated, and used to transform electrocompetent E. coli Top10 F' (Thermo Fisher). A small aliquot of the transformed cells was plated onto agar selection plates to quantify the transformation efficiency and the remaining culture was diluted in fresh 2×YT media and grown at 37° C. overnight. The following day the cells were harvested by centrifugation, resuspended in one-tenth volume of 2×YT containing 20% glycerol and aliquots were stored at −80° C. for use in subsequent superinfection-selection.

M13KO7(pIII⁻)

The helper phage M13KO7 was purchased from New England Biolabs. To generate a pIII defective derivative of M13KO7 for phagemid complementation Applicant introduced a TAA mutation at position K10 of gene 3 via site-directed mutagenesis. The phage vector was amplified with the primers M13gIII-1: 5'-CCTTCCCTCCCT-TAATCGGTTGAATG-3' (SEQ ID NO: 13) and M13gIII-2: 5'-CATTCAACCGATTAAGGGAGGGAAGG-3' (SEQ ID NO: 14) to afford the M13KO7(pIII⁻) vector.

pEDF-PylRS

To exchange the origin of replication from p15A to CloDF on the pEVOL constructs encoding tRNA$_{CUA}^{Pyl}$ and the PylRS mutants, the CloDF origin was amplified from the plasmid pCDF-1 (EMD Millipore) using the primers CloD-Fori-1: 5'-TTGGCGCGCCCAATTAGCTAGCT-CACTCGGTC-3' (SEQ ID NO: 15) and CloDFori-2: 5'-TGTTCCTAGGGATAAATTGCACTGAAATCTAG-3' (SEQ ID NO:16). The PCR product was cloned into AscI and AvrII sites that had been introduced into previously reported pEVOL-PhdRS and pEVOL-BuKRS constructs using the primers pEVOLori-1: 5'-TGTTCCTAGGTCTT-CAAATGTAGCACCTGAAG-3' (SEQ ID NO: 17) and pEVOLori-2: 5'-TTGGCGCGCCCCTTTTTCTCCTGC-CACATG-3' (SEQ ID NO: 18) to afford pEDF-PhdRS and pEDF-BuKRS, respectively.

Example 1.7. Superinfection-Selection for Amber Codon Enrichment

For the first round of superinfection-selection E. coli Top10 F' containing the naïve phagemid library were grown in 2×YT media containing 100 µg·mL⁻¹ ampicillin and 10 µg·mL⁻¹ tetracycline at 37° C. Upon reaching $OD_{600} \approx 0.3$ the expression of pIII was induced with the addition of 0.2 mM IPTG. 30 minutes after induction, the culture was superinfected with CM13 helper phage (Antibody Design Labs, 1×10¹¹ p.f.u., MOI≈15) and incubated at 37° C. for an additional 40 minutes. Following the superinfection, the cells were pelleted by centrifugation, resuspended in fresh 2×YT media containing 100 µg·mL⁻¹ ampicillin, 25 µg·mL⁻¹ kanamycin, and 1 mM IPTG, and grown at 37° C. overnight. The following day, the cells were pelleted and the plasmids purified from the cells using a commercial plasmid extraction kit (Epoch Life Sciences, Inc.). The phagemid library was separated from the helper phage and purified by agarose gel electrophoreses.

Following the first round of superinfection-selection, the phagemids were passed through E. coli DH5a to remove clones that contained nonfunctional pIII. E. coli DH5a (Lucigen) containing the M13KO7(pIII⁻) helper phage were transformed with the purified phagemid library, recovered for 1 hour in 2×YT media, and then grown overnight in 2×YT containing 100 µg·mL⁻¹ ampicillin, 25 µg·mL⁻¹ kanamycin, and 1 mM IPTG. The following day the cells were pelleted and phagemid particles were precipitated from the supernatant on ice with the addition of one-fifth volume of a 5× Phage Precipitation solution (2.5 M NaCl, 20% PEG 8,000). The precipitated particles were pelleted by centrifugation and then resuspended in one-tenth volume of PBS. The resuspension was clarified by centrifugation and the supernatant was incubated at 65° C. for 15 minutes to kill residual E. coli.

For the second round of superinfection-selection the purified phagemid particles (3.7×10⁹ c.f.u., MOI≈0.1) were added to a 100 mL culture of mid log-phase E. coli Top10 F' in 2×YT media supplemented with 10 µg·mL⁻¹ tetracycline. The culture was incubated for 1 hour at 37° C. and then diluted 1:1 with fresh 2×YT containing 100 µg·mL⁻¹ ampicillin and 0.5 mM IPTG. The culture was incubated at 37° C. to $OD_{600} \approx 0.4$ and then 60 mL was removed and infected with CM13 helper phage (1×10¹¹ p.f.u., MOI≈10). The culture was incubated for an additional 45 minutes before the cells were pelleted and resuspended in 500 mL of fresh 2×YT media supplemented with 100 µg·mL⁻¹ ampicillin, 25 µg·mL⁻¹ kanamycin, and 1 mM IPTG. The culture was then incubated at 37° C. overnight and the following day the phagemid library was extracted and purified as describe above.

Example 1.8. Phagemid Particle and Phage Quantification

For all experiments phagemid particles and phages were quantified via a colony forming unit assay. In this assay, serial dilutions of the phage solution were prepared in 2×YT media and 10 µL of each dilution was added to 90 µL of log-phase E. coli Top10 F'. Following addition of the phage dilutions, the culture was incubated at 37° C. for 45 minutes and then 10 µL was spotted onto agar selection plates containing either 100 µg·mL⁻¹ ampicillin (phagemids) or 25 µg·mL⁻¹ kanamycin (phage), which were incubated at 37° C. overnight. The following day, colonies in each spot were counted and this number was used to calculate the number of colony forming units in the solution.

Example 1.9. Phagemid Particle Expression and Purification

To express the amber-codon-obligate phagemid library with phenylalanine derivatives Applicant used a previously reported pyrrolysyl-tRNA synthetase mutant containing alanine mutations at positions N346 and C348 (PhdRS). PhdRS and its cognate tRNA (tRNA$_{CUA}^{Pyl}$) were expressed from a pEVOL plasmid containing the CloDF replication origin dubbed pEDF-PhdRS. The amber-codon-obligate library from the second round of superinfection-selection was used to transform electrocompetent E. coli Top10 containing M13KO7(pIII⁻) and pEDF-PhdRS yielding 6.92×10⁸ transformants. The transformed cells were grown to $OD_{600} \approx 0.5$ at 37° C. in 200 mL 2×YT media containing 100 µg·mL⁻¹ ampicillin, 34 µg·mL⁻¹ chloramphenicol, and 25 µg·mL⁻¹ kanamycin at which point protein expression was induced with the addition of 1 mM IPTG and 0.2% arabinose and the culture was split into two flasks. To one flask was added one of the phenylalanine derivatives 1-4 to a final concentration of 4 mM. Following induction, the temperature was changed to 30° C. and the phagemid particles were expressed for 18-24 hours.

For expressing phagemid particles with lysine derivatives Applicant used a previously reported PylRS mutant containing the Y384W mutation (BuKRS).[19] BuKRS and tRNA$_{CUA}^{Pyl}$, were expressed from a pEDF construct described above. Electrocompetent E. coli Top10 containing M13KO7(pIII⁻) and pEDF-BuKRS were transformed with the amber-codon-obligate library yielding 3.1×10⁹ transformants. Particles were expressed exactly as described for the phenylalanine derivatives but with the addition of 5 mM nicotinamide to the growth media at the time of induction.

To purify ncAA-incorporated phagemid particles, cells were pelleted by centrifugation and the upper 80 mL of media was transferred to a new tube. To the clarified media was added 20 mL of 5× Phage Precipitation solution and the mixture was incubated at 4° C. overnight. The following day, particles were pelleted by centrifugation, the supernatant was decanted, and the pellet was resuspended in 10 mL of PBS, pH 7.4. Residual cells were pelleted by centrifugation and phagemid particles were precipitated again by overnight incubation in 1× Phage Precipitation solution. Following the second precipitation, the particles were pelleted by centrifugation and the pellet resuspended in 1 mL of PBS. Residual cells were pelleted by centrifugation and the solution was incubated at 65° C. for 15 minutes to kill any remaining *E. coli*. Purified phagemid particles were quantified as described above and immediately used for selection experiments.

Example 1.10. Recombinant Protein Preparation

Sirtuin 1

*E. coli* BL21 (DE3) containing the plasmid pQE80-His$_6$-SIRT1 were grown at 37° C. in 3 L of 2×YT media supplemented with 100 μg·mL$^{-1}$ ampicillin to an OD$_{600}$ of 0.7 at which point protein expression was induced with the addition of 0.5 mM IPTG. Four hours post induction the cells were harvested by centrifugation and cell pellets were stored at −80° C. until purification.

Cell pellets were resuspended in 50 mL of lysis buffer (50 mM Tris pH 8.0, 250 mM NaCl, 10 mM imidazole, 0.1 mM phenylmethanesulfonyl fluoride (PMSF), 1% Triton X-100) and incubated with 1 mg·mL$^{-1}$ lysozyme (chicken egg white) for 30 minutes on ice. Following incubation, the resuspension was sonicated twice (1 s on, 1 s off, 1 min total, 60% output) and clarified by centrifugation. To the clarified supernatant was added 4 mL of a 50% slurry of high affinity Ni-charged resin (Genscript) and the mixture was incubated at 4° C. with end-over-end rotation for 30 minutes. After 30 minutes, the mixture was filtered through a disposable column and the resin was washed with 40 mL of lysis buffer containing 0.1% Triton X-100, followed by 40 mL of lysis buffer without Triton X-100. The bound protein was eluted with 7 mL of elution buffer (lysis buffer containing 250 mM imidazole) and the eluted protein was loaded onto a HiPrep 26/10 desalting column (GE Healthcare) that had been pre-equilibrated with Source 15Q buffer A (20 mM Tris pH 8.0, 50 mM NaCl, 0.2 mM DTT, 10% glycerol). The desalted protein was concentrated by ultrafiltration to 1 mL (10 kDa MWCO) and applied to a 10 mL Source 15Q column (GE Healthcare) pre-equilibrated with Source 15Q buffer A. The column was washed with 3 CV (2 mL min-1) of Source 15Q buffer A and then eluted with a linear gradient from 0-60% of Source 15Q buffer B (20 mM Tris pH 8.0, 1 M NaCl, 0.2 mM DTT, 10% glycerol; 1 mL·min$^{-1}$) over 5 CV. The fractions containing SIRT1 were concentrated and stored at −80° C. Enzyme concentration was determined from the absorbance at 280 nm using the calculated extinction coefficient of 40,340 M$^{-1}$·cm$^{-1}$.

Sirtuin 2

*E. coli* Top10 containing the plasmid pHEX-His$_6$-SIRT2 were grown at 37° C. in 2 L of 2×YT containing 100 μg·mL$^{-1}$ ampicillin to OD$_{600}$ of 0.6 at which point SIRT2 expression was induced by the addition of 0.1 mM IPTG. Two hours after induction the cells were harvested by centrifugation and the cell pellets were stored at −80° C. until purification.

Cell pellets were thawed and resuspended in 40 mL of lysis buffer containing 50 mM NaH$_2$PO$_4$ pH 8.0, 300 mM NaCl, 10 mM imidazole, 0.1 mM PMSF. The resuspended pellet was incubated in the presence of 1 mg·mL$^{-1}$ lysozyme for 30 minutes on ice. Following incubation, the resuspension was sonicated twice (1 s on, 1 s off, 1 min total, 60% output) and clarified by centrifugation. To the clarified supernatant was added 4 mL of a 50% slurry of high affinity Ni-charged resin (Genscript) and the mixture was incubated at 4° C. with end-over-end rotation for 30 minutes. After 30 minutes, the mixture was filtered through a disposable column, the resin was washed with 40 mL of lysis buffer, and the bound protein was eluted with 7 mL of elution buffer (lysis buffer containing 250 mM imidazole). Subsequent purification steps vary depending on whether the protein was used for biotinylation and affinity selection or inhibition assays.

For affinity selection, the eluted protein was concentrated to 1 mL by ultrafiltration (10 kDa MWCO) diluted 1:9 with Q Sepharose buffer A (50 mM NaH$_2$PO$_4$ pH 8.0, 50 mM NaCl, 0.1 mM DTT) and concentrated again to 1 mL. The concentrated sample was applied to a 25 mL Q Sepharose column (GE Healthcare) that was pre-equilibrated with Q Sepharose buffer A. The column was washed with 2 CV (2 mL·min$^{-1}$) of buffer A and the proteins were eluted with a linear gradient from 0-100% buffer B (50 mM NaH$_2$PO$_4$ pH 8.0, 1 M NaCl, 0.1 mM DTT) over 3 CV (2 mL min-1). Fractions from the main peak were combined and concentrated to 1 mL for biotinylation.

For inhibition assays, the eluted protein was loaded onto a HiPrep 26/10 desalting column (GE Healthcare) that had been pre-equilibrated with Source 15Q buffer A (20 mM Tris pH 8.0, 50 mM NaCl, 0.2 mM DTT, 10% glycerol). The desalted protein was concentrated by ultrafiltration to 1 mL (10 kDa MWCO) and applied to a 10 mL Source 15Q column (GE Healthcare) pre-equilibrated with Source 15Q buffer A. The column was washed with 3 CV (2 mL·min$^{-1}$) of Source 15Q buffer A and then eluted with a linear gradient from 0-60% Source 15Q buffer B (20 mM Tris pH 8.0, 1 M NaCl, 0.2 mM DTT, 10% glycerol; 1 mL·min$^{-1}$) over 5 CV. The fractions containing pure SIRT2 were concentrated and stored at −80° C. Enzyme concentration was determined from the absorbance at 280 nm using the calculated extinction coefficient of 32,470 M$^{-1}$·cm$^{-1}$.

Sirtuin 3

*E. coli* Top10 containing the plasmid pGEX4T-GST-SIRT3 were grown at 37° C. in 2 L of 2×YT media supplemented with 100 μg·mL$^{-1}$ ampicillin to an OD$_{600}$ of 0.6 at which point protein expression was induced with the addition of 0.2 mM IPTG. Two hours post induction the cells were harvested by centrifugation and cell pellets were stored at −80° C. until purification.

Cell pellets were resuspended in 50 mL of lysis buffer (50 mM Tris pH 7.4, 150 mM NaCl, 0.1 mM PMSF, 1% Triton X-100) and incubated in the presence of 1 mg·mL$^{-1}$ of lysozyme for 30 minutes on ice. Following incubation, the resuspension was sonicated twice (1 s on 1 s off, 1 min total, 60% output) and clarified by centrifugation. To the clarified supernatant was added 3 mL of a 50% slurry of immobilized glutathione resin (Genscript) and the mixture was incubated at 4° C. for 30 minutes with end-over-end rotation. After 30 minutes the mixture was filtered through a disposable column, and the resin was washed with 50 mL of lysis buffer containing 0.1% Triton X-100. After washing, the bound protein was eluted with 10 mL of lysis buffer containing 10 mM of reduced glutathione without Triton X-100. The elution was directly applied to a HiPrep 26/10 desalting column (GE Healthcare) that had been pre-equilibrated with 50 mM Tris pH 7.5, 150 mM NaCl, 0.2 mM DTT, and 10% glycerol. The desalted protein was concentrated and stored at −80° C. Enzyme concentration was determined from the absorbance at 280 nm using the calculated extinction coefficient of 80,790 M$^{-1}$·cm$^{-1}$.

Example 1.11. Biotinylation of Sirtuin 2

SIRT2 (53 μM), in PBS pH 7.4, was biotinylated with a 10-fold molar excess of EZ-Link™ NHS-Biotin (Thermo Fisher Scientific) for 2 hours on ice with gentle rocking. After the reaction the solution was directly loaded onto a Superdex 75 10/300 GL size exclusion column (GE Healthcare) pre-equilibrated with 50 mM Tris pH 8.0, 250 mM NaCl, 0.2 mM DTT, 10% glycerol. The eluted protein was concentrated by ultrafiltration (10 kDa MWCO), flash frozen, and stored at −80° C. Biotinylation of the protein was confirmed by capture on magnetic streptavidin beads (Genscript) followed by SDS-PAGE and Coomassie staining, using 2 µg of biotinylated SIRT2, as described previously.

Example 1.12. Affinity Selection Against Streptavidin

Lyophilized streptavidin (Chem-Impex International, Inc.) was dissolved in 0.1 M NaHCO$_3$, pH 8.6 to a concentration of 25 µg·mL$^{-1}$. 1.5 mL of the protein solution was used to coat a polystyrene petri dish (60×15 mm) by incubation at 4° overnight in a sealed, humidified box. After removing the protein solution, the plate was blocked with 0.1 M NaHCO$_3$ containing 5 mg·mL$^{-1}$ BSA and 0.1 µg·mL$^{-1}$ streptavidin for 2 hours at 4° C. The plate was washed six times with 2 mL of PBST (PBS containing 0.1% Tween-20, pH 7.5) and then the purified phage library ($2 \times 10^{10}$-$4 \times 10^{11}$ c.f.u.) was incubated with the target at room temperature for 1 hour (rounds 1-3) or 30 minutes (round 4). After incubation with the ncAA-incorporated phagemid particles, the plate was washed 10 times with PBST, and the bound phagemid particles were competitively eluted by incubating with a 1 mL solution of 0.1 mM D-biotin for 30 minutes.

Example 1.13. Affinity Selection Against Sirtuin 2

For affinity selections, biotinylated SIRT2 was immobilized by capture on streptavidin coated magnetic beads (rounds 1 and 3) or neutravidin coated polystyrene plates (round 2). For selection rounds 1 and 3, 100 µL of streptavidin coated magnetic beads (50% slurry, GenScript) were washed twice with PBS and then divided into two tubes. To one tube was added biotinylated SIRT2 (10 µg) in 400 µL PBS, to the other tube was added an equivalent volume of buffer. Both tubes were incubated at room temperature for 20 minutes. After incubation, the supernatant was removed and the beads were blocked with 1 mL of 0.1 M NaHCO$_3$ pH 8.6, containing 5 mg·mL$^{-1}$ BSA for 30 minutes, at room temperature, with rotation. After blocking, the supernatant was removed from the tube without SIRT2, the beads were washed three times with PBST and once with PBS, and a negative selection was performed by incubating the beads with the purified phage library ($2.9 \times 10^{10}$-$6.2 \times 10^{10}$ c.f.u.) in 1 mL of PBS for 30 minutes, with slow rotation. Following the negative selection, the beads were pelleted and the supernatant was transferred to the beads containing SIRT2 that had been washed as described above. The phage library was incubated with the immobilized target at room temperature, for 30 minutes, with rotation. Following the selection, the supernatant was removed and the beads were washed ten times with PBST. The beads were transferred to a new tube after the third, sixth, and ninth washes to remove phagemid particles displaying peptides that bind to the polypropylene tubes. Following washing, the bound particles were eluted by incubating in 100 L of 50 mM glycine pH 2.2 for exactly 10 minutes. After 10 minutes, the supernatant was removed and neutralized with 50 µL of 1 M Tris pH 8.0.

For selection round 2, eight wells of a pre-blocked neutravidin coated polystyrene plate (Pierce) were washed three times with 250 µL PBS and then biotinylated SIRT2 (1.25 µg), in 100 µL PBS, was added to each of the wells. The plate was incubated at room temperature for 30 minutes in a sealed, humidified box to allow for capture of the biotinylated SIRT2 target. The wells were then washed three times with PBST followed by once with PBS and the phage library ($5.4 \times 10^9$ c.f.u.) in 800 µL PBS was divided evenly among the wells. The phagemid particles were incubated with the immobilized target for 30 minutes and then the supernatant was removed and each of the wells washed ten times with 250 µL PBST. Following washing, the bound phagemid particles were eluted by incubating in 100 µL of 50 mM glycine pH 2.2 for exactly 10 minutes. After 10 minutes, the eluted particles from each well were pooled and neutralized with 400 µL 1 M Tris pH 8.0.

Example 1.14. Phagemid Amplification

Following each round of selection, the eluted phagemid particles were amplified by passage through *E. coli* Top10 containing the M13KO7(pIII$^-$) helper phage and the plasmids pEDF-PhdRS for incorporating mBrF or pEDF-BuKRS for incorporating BuK. 10 µL of the eluted phagemid particles was reserved for tittering and the remaining solution was used to infect a 20 mL culture of *E. coli* Top10 F' for 45 minutes at 37° C. Following infection, the cells were pelleted and resuspended in 100-300 mL of 2×YT media containing 100 µg·mL$^{-1}$ ampicillin and amplified overnight at 37° C. The following day, the phagemid library was purified using a commercial plasmid extraction kit, and the purified library was used to transform electrocompetent *E. coli* Top10 containing M13KO7(pIII$^-$) and the appropriate pEDF-aaRS construct. A small portion of the transformation was tittered to ensure that the number of transformants exceeded the number of phagemid particles eluted in the previous round by at least 100-fold. Transformed cells were directly used to express phagemid particles for further rounds of selection.

Example 1.15. Molecular Dynamics Simulations

General Information

The protein environments after the reaction of the peptide with NAD$^+$ were studied by simulating the different peptides interacting in the position of an analogous inhibitor based on the crystal structure PDB 4×30. The Schrödinger (Release 2017-4) 39 and Desmond software was used for all simulations. Each of the simulations for investigating the protein-peptide interactions followed the steps described below.

Protein Preparation Module

Several structures of SIRT2 were available in the PDB. By overlaying these entries it was evident that SIRT2 is a conformationally flexible protein due to its many loops. However, the domain where the peptide inhibitors bind is a somewhat inflexible region. The 4×30 crystal structure was chosen as a template structure because it contained an analogous thiomyristoyl-lysine peptide, which was modified to the target peptides (S2P03, S2P04, S2P07, S2P04-5, and Ac-S2P04-5), and because it had the fewest missing residues with the highest resolution among the crystal structures available. The Protein Preparation Wizard in the Schrödinger software was used to prepare the 4x3O.pdb structure for simulation at a pH of 7.5±0. Crystal structure waters were maintained. The PrimeLoop algorithm was used to fill in missing residues (Met299-Gly304). After initial preparation, the H-bonding network was optimized using the PROPKA tool at a pH of 7.5±0, water molecule orientations were sampled, and a restrained minimization was performed on all atoms using the OPLS3 force-field.

System Builder Module: Preparation of the Molecular Dynamics Simulations

The System Builder tool within the Desmond Module (note that this is in the Schrödinger Software Maestro interface distributed with Desmond) was used to prepare the model for a Desmond MD-simulation. Modifications by transforming the native thiomyristoyl-lysine peptide into the target peptides were made before applying the solvent box. An orthorhombic solvent box was constructed with a distance of 10.0 Å around the peptide-protein assembly. The solvent box was size-minimized before applying explicit water molecules to the system. The TIP4P water model was used for the explicit water molecules and the OPLS3 force-field for all other atoms. The protein-peptide assembly was charge neutralized using a physiological NaCl concentration of 0.15 M.

Desmond Module: Molecular Dynamics Simulations

The Desmond multisim molecular dynamics protocol was used for all runs using the NPT ensemble (1.0135 bar, 310.15 K) for a 10 ns production run taking a snapshot every 10 ps, resulting in a trajectory with 1000 frames. The system was put through a relaxation protocol before the production run, as implemented in the Desmond Schrödinger software Maestro interface and outlined below:
1. Restrained minimization steps
2. Brownian Dynamics NVT, T=10 K, small time steps, and restraints on solute heavy atoms, 100 ps
3. NVT, T=10 K, small time steps, and restraints on solute heavy atoms, 12 ps
4. NPT, T=10 K, and restraints on solute heavy atoms, 12 ps
5. NPT and restraints on solute heavy atoms, 12 ps
6. NPT and no restraints, 24 ps
7. Production run Protein-Peptide Interaction Charts The MD-simulation results were imported and ligand interaction tables were then generated using the Ligand Interaction Diagram module in the Desmond distributed Schrödinger software. The results show only the hydrophobic interactions stemming from the residues adjacent to the thBuK residue in the peptide inhibitor. The accompanying plots show which of the 1000 frames the interactions occur (orange bar).

Example 1.16. Peptide Synthesis

Peptides were synthesized via manual Fmoc-based solid-phase peptide synthesis on Rink-amide resin using N,N,N',N'-tetramethyl-O-(1H-benzotriazol-1-yl) uranium hexafluorophosphate (HBTU) as a coupling agent. Rink-amide MBHA resin (Novabiochem, 100 mg, substitution: 0.78 mmol g$^{-1}$) was swelled for 1 hour in 10 mL of DMF. Deprotection, coupling, and cleavage reactions were carried out at room temperature in a glass reaction vessel agitated with end-over-end rotation under the following conditions:

Deprotection

A solution of 20% piperidine in DMF (v:v, 5 mL) was added to the swelled resin for 5 minutes. The resin was washed (3×5 mL DMF) and the deprotection reaction was repeated for 15 minutes. After the second deprotection reaction the resin was washed again (5×5 mL DMF, 2×5 mL DCM).

Coupling

Each coupling reaction contained the Fmoc-protected amino acid (312 µmol, 4 eq.), HBTU (304.2 µmol, 3.9 eq.), and N,N-diisopropylethylamine (DIPEA, 780 µmol, 10 eq.) dissolved in 5 mL DMF. The Fmoc-protected amino acid was pre-activated with HBTU and DIPEA for 5 minutes before being adding to the resin for 40 minutes. After 40 minutes the resin was washed (5×5 mL DMF, 2× 5 mL DCM).

N-Terminal Acetylation

For synthesizing Ac-S2P04-5 with an N-terminal acetyl modification, the resin was washed (5×5 mL DMF, 3× 5 mL DCM) following the last Fmoc deprotection and then incubated with a solution of acetic anhydride, pyridine, and DMF (1:2:3, v:v:v) for 1 hour at room temperature with rotation. The peptide was then cleaved and simultaneously sidechain deprotected as described below.

Cleavage and Deprotection

After the final Fmoc deprotection, the resin was washed (5×5 mL DMF, 5×5 mL DCM) and the peptide was cleaved from the resin and simultaneously sidechain deprotected using 7 mL of a cleavage cocktail containing 88% trifluoroacetic acid (TFA), 5% phenol, 5% H$_2$O, and 2% triisopropylsilane (v:w:v:v) for two hours under a blanket of nitrogen. After two hours, the resin was filtered and washed (2×1 mL cleavage cocktail) and the combined filtrate was reduced to ~4 mL using a stream of nitrogen. The concentrated solution was added dropwise to cold diethyl ether (40 mL) and incubated on ice for 10 minutes. The precipitated peptide was collected by centrifugation, washed twice with cold diethyl ether (20 mL), dried under a stream of nitrogen, and stored at −20° C.

Purification

Crude peptides were dissolved in DMF and purified by semi-preparative RP-HPLC on a C18 column (Alltech, 10×250 mm, 10 µm, 100 Å pore or Supelco, 10×250 mm, 5 µm, 300 Å pore). Solvent A: water with 0.1% TFA, Solvent B: acetonitrile with 0.1% TFA. The peptides were eluted with a linear gradient from 20-50% Solvent B over 30 minutes. Fractions containing the purified peptides were combined and lyophilized to afford a fluffy white powder. Masses of the peptides were confirmed by MALDI-TOF mass spectrometry. Peptide purity was determined according to the HPLC traces at 215 nm and was greater than 90% for all peptides used.

Example 1.17. Sirtuin Inhibition Assay

Inhibition assays for SIRT1-3 were performed using a recently reported fluorogenic, universal sirtuin substrate (JPT Peptide Technologies, GmbH). The inhibition reactions were performed in 50 µL volumes at 37° C. in black, half-area, 96-well plates. The sirtuin enzyme (0.25 µM) was pre-incubated with different concentrations of the synthetic peptides (0.0064-50 µM for SIRT1 and SIRT2, 0.5-100 µM for SIRT3) or TB (0.16-150 µM for SIRT1-3) and 1 mM NAD$^+$ in assay buffer (20 mM Tris pH 7.8, 150 mM NaCl, 5 mM MgCl$_2$, 1 mM DTT) for 15 minutes. Following incubation, the reaction was started with the addition of the substrate (5 µM) and product formation was monitored by measuring the fluorescence intensity every 20 seconds for 5 minutes (SIRT2) or 30 minutes (SIRT1 and SIRT3) in a BioTek Synergy H1 microplate reader at $\lambda_{Ex}$=320 nm, $\lambda_{Em}$=408 nm (gain=130, read height=7 mm). Initial rates of product formation were determined by linear regression of the plot of fluorescence intensity versus time and normalized relative to 0% activity (max inhibitor) and 100% activity (no inhibitor) controls. IC$_{50}$ values were determined by nonlinear regression of the plot of normalized initial rate versus inhibitor concentration using GraphPad Prism.

Example 1.18. Cell Cultures and Western Blotting

MCF-7 (HTB-22) and HEK 293T (CRL-11268) cells purchased from American Type Culture Collection were grown in Dulbecco's Modified Eagle Medium (Invitrogen) containing 10% fetal bovine serum (Invitrogen) at 37° C. in an atmosphere of 5% $CO_2$. Cells were seeded in a 6-well plate (Falcon 353046) at $5\times10^5$ viable cells/well, and grown for 24-48 hours to 60-70% confluence. The media was aspirated and replaced with one containing 50 µM of the synthetic peptide, TB, or a vehicle control (0.25% DMF). After incubating with the inhibitors for 24 hours, the media was removed and the cells were washed twice with ice-cold PBS (Invitrogen). Cells were lysed on ice for 30 minutes in 100 µL of buffer containing 25 mM Tris pH 7.4, 150 mM NaCl, 10% glycerol, 4 mM $MgCl_2$, 0.2 mM DTT, 1% NP-40, 25 mM nicotinamide, 5 µM trichostatin A, and 1:100 dilution of protease inhibitor cocktail (Sigma-Aldrich). The lysates were clarified by centrifugation, quantified by BCA assay (Pierce), and aliquots were stored at −80° C. Cell lysates (15 or 20 µg) were resolved by SDS-PAGE under denaturing conditions on a 12% acrylamide gel and then transferred to a 0.2 µm nitrocellulose membrane (Bio-Rad). α-tubulin acetylation (K40) and total a-tubulin were probed with primary antibody clones 6-11B-1, and B-5-1-2, respectively, which were purchased from Sigma-Aldrich (1:2,000 dilution). Primary antibodies were probed with HRP-conjugated goat anti-mouse IgG (Jackson ImmunoResearch Laboratories, Inc., 1:10,000 dilution). Chemiluminescence signals were generated with the SuperSignal™ ELISA Pico Chemiluminescent substrate (ThermoFisher Scientific) and visualized with a Bio-Rad ChemiDoc XRS+ imaging system.

Example 2. Identification of ENL Inhibitors

Acute myeloid leukemia (AML), a disease characterized by uncontrolled proliferation of abnormal myeloblast, is the most commonly diagnosed and the deadliest subtype of leukemia. In the United States, every year an estimated 21,450 people will be diagnosed with AML and 10,920 people will die from the disease, making up almost half of all deaths from all subtypes of leukemia.

It has been shown that the survival of several types of AML cells is related to ENL, an epigenetic reader of histone. ENL protein binds to acylated histone H3 through its N-terminal YEATS domain and then recruits RNA polymerase II to the oncogenes, which are highly expressed in leukemia cells. Knockout or mutations of ENL protein in leukemia cells have a significant suppression on their growth and increase their differentiation.

Therefore, if the binding of ENL to acetylated histones is inhibited, the transcription of oncogenic genes in leukemia cells should be downregulated, which leads to a potential targeted therapy for AML. In this Example, Applicant describes a phage-assisted, active site-directed ligand evolution technique that can readily screen out potential inhibitors with nanomolar affinities.

Peptide-based inhibitors, superior to small molecules, provide satisfying affinity and selectivity toward binding to proteins that involve large, relatively flat surfaces. Peptides are also easy to screen. For instance, using phage display techniques, it is possible for a single researcher to screen a library of greater than 1010 unique peptides in a matter of days.

However, since phage-displayed peptides are expressed in *Escherichia coli*, this limits the coding capacity of the bacterial translation to 20 canonical amino acid (cAA) building blocks, capping both sequence and chemistry that can be explored. Furthermore, traditional phage display often relies on the usage of a randomized library and is generally agnostic to any known protein-ligand interactions, which can be limited in the ability to mimic strong interactions.

Figure 7A:
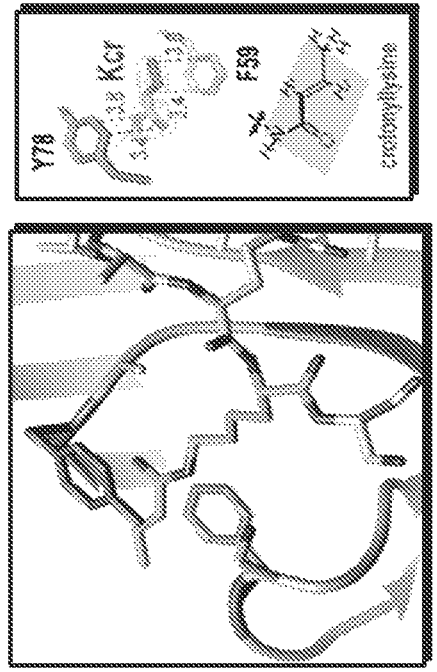
FIG. 7A provides a diagram that illustrates the interaction between a protein target and a ligand.
Figure 7B:
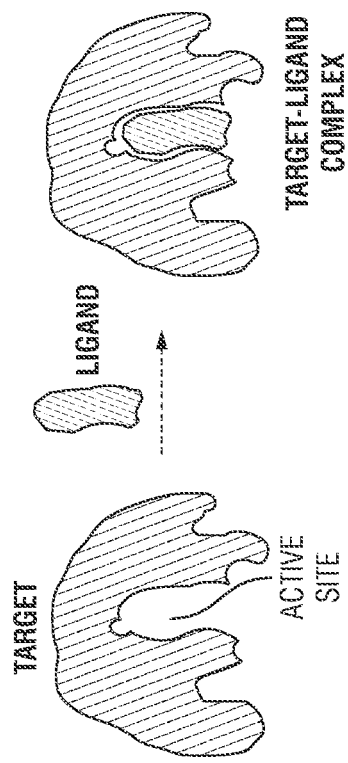
FIG. 7B shows the genetic incorporation of a ligand-fused ncAA into phage-displayed peptides for active site-directed binding to a protein target that is followed by stringent wash and elution to select high-affinity and selective phages.

Thus, to expand the chemical diversity of the library and exploit unique chemical interactions unafforded to the 20 cAAs, Applicant incorporated a non-canonical amino acid (ncAA) into a phage display system. The proposed phage-assisted, active site-directed ligand evolution approach is shown in FIGS. 7A-B, where a warhead with known capabilities to bind the target protein is installed in an ncAA, which can be genetically incorporated into a phage-displayed sequence-randomized peptide library. In the phage-displayed peptides, the warhead is expected to interact with the binding site and serve as an anchor to bind to the ligand-binding cavity of the target enzyme while the amino acid residues flanking the ligand-fused ncAA provide additional interactions at the peptide binding groove for improved affinity and selectivity.

Figure 7C:
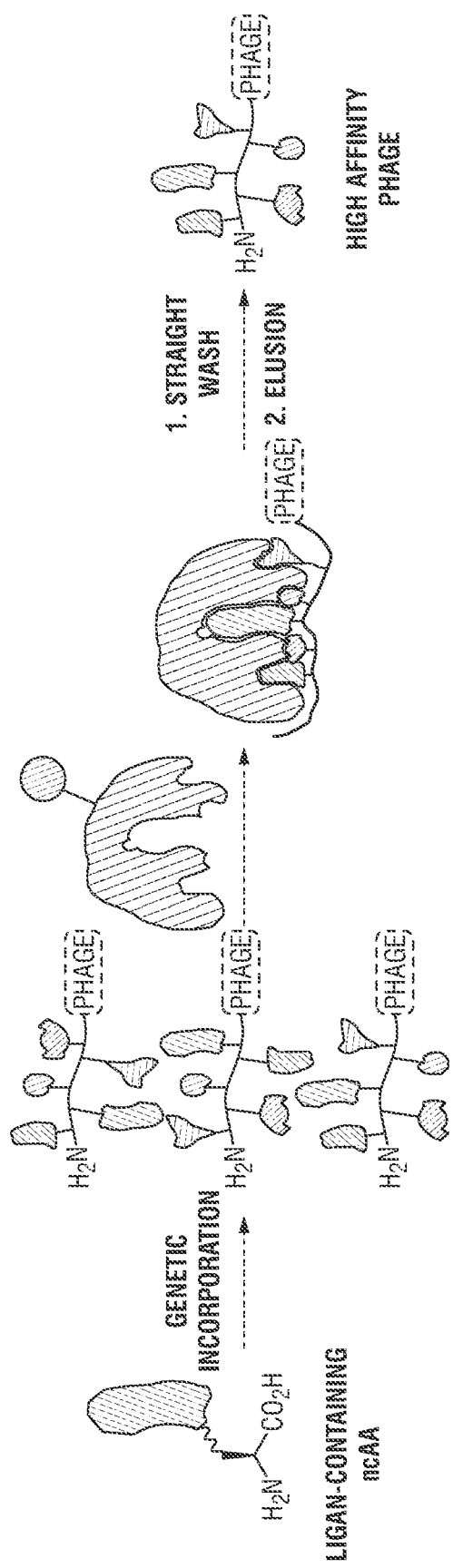
FIG. 7C shows a crystal structure of a H3K9cr peptide complexed to ENL from PDB entry 5HJB. The CrK, cyan, is complexed between F59 and Y78, green.

Recent studies have found that two aromatic residues, F59 and Y78, in the ligand-binding site of the YEATS domain can form a π-π-π stacking interaction with the conjugated π system of $N^\epsilon$-crotonyllysine (CrK, FIG. 7C). Inspired by this discovery, Applicant decided to incorporate CrK into the phage display system described in Example 1 and exploit the π-π-π interaction generated by the ncAA to guide the peptide library to the active site of YEATS domain-containing proteins.

In this Example, Applicant first constructed a 21 base-pair DNA library that encodes 7 randomized amino acids from NNK triplet nucleotides. To genetically incorporate CrK, Applicant applied a superinfection immunity-based technique described in Example 1 for the construction of an amber obligate phagemid library. The resulting amber obligate library can be expressed using the PylRS amber suppression system Applicant previously evolved (ACS chemical biology 2013, 8 (8), 1664-70).

To demonstrate the active site ligand evolution concept, the displayed peptide library was panned against ENL that has been biotinylated and immobilized on streptavidin-coated magnetic beads. Once bound to the target protein, the expressed peptide library was washed to remove nonspecific binding and eluted with an acidic denaturing condition and amplified in *E. coli*. The selection process was carried out four times to screen out high affinity and selective inhibitors. Over four rounds of selection, the phage yield increased significantly with a 540-fold difference between the first and fourth round.

Figure 8B:
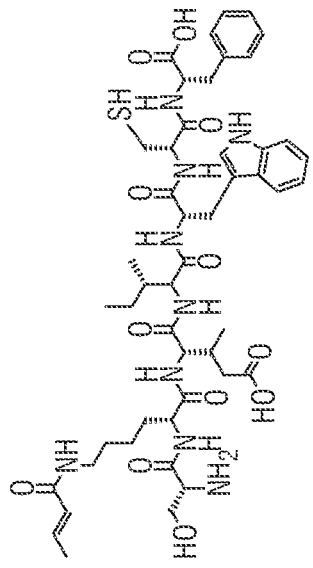
FIG. 8B shows the structure of 7CrKEnl2 (SEQ ID NO: 7) selected from phage display.
Figure 8D:
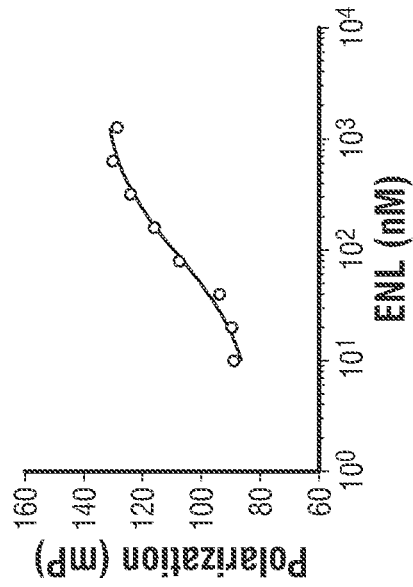
FIG. 8D shows the fluorescence polarization analysis of 5-FAM conjugated 7CrkENL2 binding to ENL. The percentages of the ligands from first and final round, enrich ratio and dissociation constants ($K_d$) for both ligands are shown in the table.
Figure 8A:
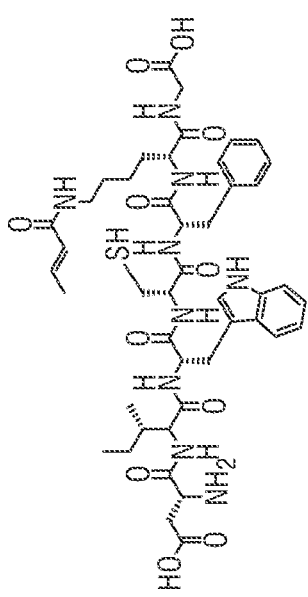
FIG. 8A shows the structure of 7CrKEnl1 (SEQ ID NO:6) selected from phage display.
Figure 8C:
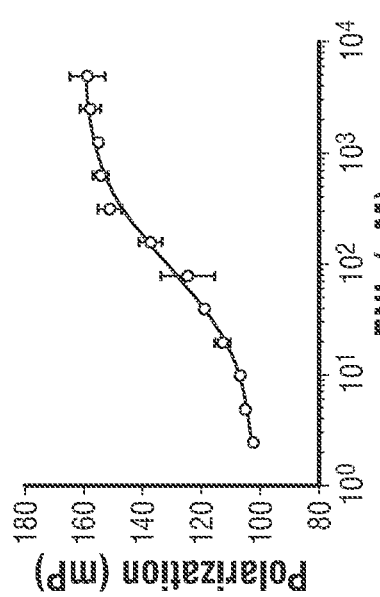
FIG. 8C shows the fluorescence polarization analysis of 5-FAM conjugated 7CrkENL1 binding to ENL.

Additionally, after four rounds of selection, the library regions were analyzed using Illumina Next-Generation sequencing. This gave two strong consensus sequences, 7CrKEnl1 and 7CrKEnl2 (FIGS. 8A-B) that consisted of 98% of total phages after the fourth round of selection with a 540-fold and a 300-fold enrichment, respectively, between the first and fourth rounds. To determine the affinity of 7CrKEnl1 and 7CrKEnl2 to ENL, Applicant synthesized 5-FAM-conjugated peptides and then characterized their bindings to ENL using the fluorescence polarization analysis. The results indicated a 94 nM dissociation constant for 7CrKEnl1 and 90 nM for 7CrKEnl2 (FIGS. 8C-D). Collectively, results in FIG. 8 demonstrated a successful application of using our genetically encoded, phage-assisted, active site-directed ligand evolution in identifying a potent peptide inhibitor for a therapeutic protein target.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of constructing a phage display library, said method comprising:
   (a) providing a naïve phage display library,
      wherein the naïve phage display library is a heptapeptide library that comprises a plurality of nucleic acids that encode a phage coat protein gene,
      wherein the phage coat protein gene comprises seven randomized (NNK) codons fused to its N-terminus, and
      wherein the combinatorial regions of at least some of the nucleic acids comprise at least one in-frame amber codon;
   (b) transforming the naïve phage display library into bacterial host cells;
   (c) inducing expression of the phage coat protein gene in the transformed bacterial host cells,
      wherein the expression of the phage coat protein from nucleic acids that only contain in-frame sense codons in the phage coat protein gene renders the bacterial host cells immune to infection by a helper phage;
   (d) infecting the transformed bacterial host cells with the helper phage,
      wherein the helper phage encodes and expresses a gene that renders the infected bacteria resistant to an antibiotic;
   (e) growing the infected and uninfected bacterial host cells in a medium containing the antibiotic,
      wherein the growing results in the selection of the infected bacteria, and
      wherein the infected bacteria comprise the helper phage and at least some of the nucleic acids comprising the phage coat protein gene with the at least one in-frame amber codon in the combinatorial region;
   (f) extracting the nucleic acids from the bacterial cell host cells;
   (g) transforming the extracted nucleic acids into amber-suppressing bacterial host strains,
      wherein the amber-suppressing bacterial host strains are co-infected with a knockout helper phage that does not express the phage coat protein gene, and
      wherein the transforming allows for the selective production of phage particles from cells harboring nucleic acids comprising the phage coat protein gene with the at least one in-frame amber codon in the combinatorial region; and
   (h) purifying the nucleic acids from the produced phage particles to provide the phage display library,
      wherein at least 90% of the combinatorial regions in the phage display library comprise at least one in-frame amber codon.

2. The method of claim 1, wherein more than 90% of the combinatorial regions in the phage display library comprise at least one in-frame amber codon.

3. The method of claim 1,
- wherein the naïve phage display library is prepared by site-directed mutagenesis,
- wherein the phage display library comprises a plurality of phages, phagemids, or combinations thereof, and wherein the plurality of nucleic acids in the phage display library comprise the nucleic acids of the phages or phagemids,
- wherein the combinatorial region encodes a peptide or a protein, and
- wherein the combinatorial region in at least some of the nucleic acids in the phage display library comprise a plurality of in-frame amber codons, wherein the plurality of in-frame amber codons are randomly distributed throughout the combinatorial region.

4. The method of claim 1,
- wherein the bacterial host cells comprise *E. coli* bearing an F sex pilus,
- wherein the phage coat protein gene is the PIII gene,
- wherein the phage coat protein gene is positioned near an IPTG-inducible promoter, and wherein the phage coat protein is expressed by exposing the bacterial host cells to IPTG,
- wherein the helper phage is a CM13 helper phage, and
- wherein the helper phage encodes and expresses a gene that renders the infected bacteria resistant to kanamycin.

* * * * *

```
                            SEQUENCE LISTING

<160> NUMBER OF SEQ ID NOS: 68

<210> SEQ ID NO 1
    <211> LENGTH: 7
    <212> TYPE: PRT
    <213> ORGANISM: Artificial Sequence
    <220> FEATURE:
    <223> OTHER INFORMATION: Sirtuin 2 Inhibitor
    <220> FEATURE:
    <221> NAME/KEY: MISC_FEATURE
    <222> LOCATION: (4)..(4)
    <223> OTHER INFORMATION: X is a Non-Canonical Amino Acid

<400> SEQUENCE: 1

Cys Thr Val Xaa Thr Ser Leu
    1               5

<210> SEQ ID NO 2
    <211> LENGTH: 7
    <212> TYPE: PRT
    <213> ORGANISM: Artificial Sequence
    <220> FEATURE:
    <223> OTHER INFORMATION: Sirtuin 2 Inhibitor
    <220> FEATURE:
    <221> NAME/KEY: MISC_FEATURE
    <222> LOCATION: (5)..(5)
    <223> OTHER INFORMATION: X is a Non-Canonical Amino Acid

<400> SEQUENCE: 2

Thr Cys Thr Val Xaa Ile Gly
    1               5

<210> SEQ ID NO 3
    <211> LENGTH: 7
    <212> TYPE: PRT
    <213> ORGANISM: Artificial Sequence
    <220> FEATURE:
    <223> OTHER INFORMATION: Sirtuin 2 Inhibitor
    <220> FEATURE:
    <221> NAME/KEY: MISC_FEATURE
    <222> LOCATION: (4)..(4)
    <223> OTHER INFORMATION: X is a Non-Canonical Amino Acid

<400> SEQUENCE: 3

Cys Thr Phe Xaa Val Pro Thr
    1               5

<210> SEQ ID NO 4
    <211> LENGTH: 5
    <212> TYPE: PRT
    <213> ORGANISM: Artificial Sequence
    <220> FEATURE:
    <223> OTHER INFORMATION: Sirtuin 2 Inhibitor
    <220> FEATURE:
    <221> NAME/KEY: MISC_FEATURE
    <222> LOCATION: (4)..(4)
    <223> OTHER INFORMATION: X is a Non-Canonical Amino Acid
```

```
<400> SEQUENCE: 4

Cys Thr Val Xaa Ile
1               5

<210> SEQ ID NO 5
<211> LENGTH: 5
<212> TYPE: PRT
<213> ORGANISM: Artificial Sequence
<220> FEATURE:
<223> OTHER INFORMATION: Sirtuin 2 Inhibitor
<220> FEATURE:
<221> NAME/KEY: MISC_FEATURE
<222> LOCATION: (1)..(1)
<223> OTHER INFORMATION: X is a Non-Canonical Amino Acid or Aminobutyric
      Acid
<220> FEATURE:
<221> NAME/KEY: MISC_FEATURE
<222> LOCATION: (4)..(4)
<223> OTHER INFORMATION: X is a Non-Canonical Amino Acid

<400> SEQUENCE: 5

Xaa Thr Val Xaa Ile
1               5

<210> SEQ ID NO 6
<211> LENGTH: 7
<212> TYPE: PRT
<213> ORGANISM: Artificial Sequence
<220> FEATURE:
<223> OTHER INFORMATION: SNL Inhibitor
<220> FEATURE:
<221> NAME/KEY: MISC_FEATURE
<222> LOCATION: (6)..(6)
<223> OTHER INFORMATION: X is a Non-Canonical Amino Acid

<400> SEQUENCE: 6

Asp Ile Trp Cys Phe Xaa Gly
1               5

<210> SEQ ID NO 7
<211> LENGTH: 7
<212> TYPE: PRT
<213> ORGANISM: Artificial Sequence
<220> FEATURE:
<223> OTHER INFORMATION: SNL Inhibitor
<220> FEATURE:
<221> NAME/KEY: MISC_FEATURE
<222> LOCATION: (2)..(2)
<223> OTHER INFORMATION: X is a Non-Canonical Amino Acid

<400> SEQUENCE: 7

Ser Xaa Asp Ile Trp Cys Phe
1               5

<210> SEQ ID NO 8
<211> LENGTH: 21
<212> TYPE: DNA
<213> ORGANISM: Artificial Sequence
<220> FEATURE:
<223> OTHER INFORMATION: Partial Plasmid Encoding the Amber-Codon-
      Obligate Peptide-pIII Library
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
```

```
<222> LOCATION: (7)..(8)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
<223> OTHER INFORMATION: n is a, c, g, or t

<400> SEQUENCE: 8
nnknnknnkn nknnknnknn k                                     21

<210> SEQ ID NO 9
<211> LENGTH: 5
<212> TYPE: PRT
<213> ORGANISM: Artificial Sequence
<220> FEATURE:
<223> OTHER INFORMATION: S2P04-5
<220> FEATURE:
<221> NAME/KEY: MISC_FEATURE
<222> LOCATION: (4)..(4)
<223> OTHER INFORMATION: X is a Non-Canonical Amino Acid

<400> SEQUENCE: 9

Cys Thr Val Xaa Ile
1               5

<210> SEQ ID NO 10
<211> LENGTH: 5
<212> TYPE: PRT
<213> ORGANISM: Artificial Sequence
<220> FEATURE:
<223> OTHER INFORMATION: S2P04(Abu)-5
<220> FEATURE:
<221> NAME/KEY: MISC_FEATURE
<222> LOCATION: (1)..(1)
<223> OTHER INFORMATION: X is Abu
<220> FEATURE:
<221> NAME/KEY: MISC_FEATURE
<222> LOCATION: (4)..(4)
<223> OTHER INFORMATION: X is a Non-Canonical Amino Acid

<400> SEQUENCE: 10

Xaa Thr Val Xaa Ile
1               5

<210> SEQ ID NO 11
<211> LENGTH: 46
<212> TYPE: DNA
<213> ORGANISM: Artificial Sequence
<220> FEATURE:
<223> OTHER INFORMATION: pADL-g3-P1 Primer
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (19)..(20)
```

```
<223> OTHER INFORMATION: n is a, c, g, or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t

<400> SEQUENCE: 11
catgccatgg ccnnknnknn knnknnknnk nnkgcggcga aagcgg                    46

<210> SEQ ID NO 12
<211> LENGTH: 23
<212> TYPE: DNA
<213> ORGANISM: Artificial Sequence
<220> FEATURE:
<223> OTHER INFORMATION: pADL-g3-P2 Primer

<400> SEQUENCE: 12
catgccatgg ccggctgggc cgc                                             23

<210> SEQ ID NO 13
<211> LENGTH: 26
<212> TYPE: DNA
<213> ORGANISM: Artificial Sequence
<220> FEATURE:
<223> OTHER INFORMATION: M13gIII-1 Primer

<400> SEQUENCE: 13
ccttccctcc cttaatcggt tgaatg                                          26

<210> SEQ ID NO 14
<211> LENGTH: 26
<212> TYPE: DNA
<213> ORGANISM: Artificial Sequence
<220> FEATURE:
<223> OTHER INFORMATION: M13gIII-2 Primer

<400> SEQUENCE: 14
cattcaaccg attaagggag ggaagg                                          26

<210> SEQ ID NO 15
<211> LENGTH: 32
<212> TYPE: DNA
<213> ORGANISM: Artificial Sequence
<220> FEATURE:
<223> OTHER INFORMATION: CloDFori-1 Primer

<400> SEQUENCE: 15
ttggcgcgcc caattagcta gctcactcgg tc                                   32

<210> SEQ ID NO 16
<211> LENGTH: 32
<212> TYPE: DNA
<213> ORGANISM: Artificial Sequence
<220> FEATURE:
<223> OTHER INFORMATION: CloDFori-2 Primer

<400> SEQUENCE: 16
```

```
tgttcctagg gataaattgc actgaaatct ag                                    32
```

<210> SEQ ID NO 17
<211> LENGTH: 32
<212> TYPE: DNA
<213> ORGANISM: Artificial Sequence
<220> FEATURE:
<223> OTHER INFORMATION: pEVOLori-1 Primer

<400> SEQUENCE: 17

```
tgttcctagg tcttcaaatg tagcacctga ag                                    32
```

<210> SEQ ID NO 18
<211> LENGTH: 31
<212> TYPE: DNA
<213> ORGANISM: Artificial Sequence
<220> FEATURE:
<223> OTHER INFORMATION: pEVOLori-2 Primer

<400> SEQUENCE: 18

```
ttggcgcgcc ccttttttct cctgccacat g                                     31
```

<210> SEQ ID NO 19
<211> LENGTH: 21
<212> TYPE: DNA
<213> ORGANISM: Artificial Sequence
<220> FEATURE:
<223> OTHER INFORMATION: In-Frame Amber Codon Fragment from Phage
      Display

<400> SEQUENCE: 19

```
tcgttgtagt tgcagcattc t                                                21
```

<210> SEQ ID NO 20
<211> LENGTH: 21
<212> TYPE: DNA
<213> ORGANISM: Artificial Sequence
<220> FEATURE:
<223> OTHER INFORMATION: In-Frame Amber Codon Fragment from Phage
      Display

<400> SEQUENCE: 20

```
tagagtgcta ttacgtattg t                                                21
```

<210> SEQ ID NO 21
<211> LENGTH: 21
<212> TYPE: DNA
<213> ORGANISM: Artificial Sequence
<220> FEATURE:
<223> OTHER INFORMATION: In-Frame Amber Codon Fragment from Phage
      Display

<400> SEQUENCE: 21

```
atttagattc atccgtattt t                                                21
```

<210> SEQ ID NO 22
<211> LENGTH: 21
<212> TYPE: DNA
<213> ORGANISM: Artificial Sequence
<220> FEATURE:
<223> OTHER INFORMATION: In-Frame Amber Codon Fragment from Phage
      Display

<400> SEQUENCE: 22

```
tatagtatta agtggtaggt t                                                21
```

```
<210> SEQ ID NO 23
<211> LENGTH: 21
<212> TYPE: DNA
<213> ORGANISM: Artificial Sequence
<220> FEATURE:
<223> OTHER INFORMATION: In-Frame Amber Codon Fragment from Phage
      Display

<400> SEQUENCE: 23
ggtgcgtaga ggccggggat g                                             21

<210> SEQ ID NO 24
<211> LENGTH: 21
<212> TYPE: DNA
<213> ORGANISM: Artificial Sequence
<220> FEATURE:
<223> OTHER INFORMATION: In-Frame Amber Codon Fragment from Phage
      Display

<400> SEQUENCE: 24
cgtatgcatt aggcgttttt t                                             21

<210> SEQ ID NO 25
<211> LENGTH: 21
<212> TYPE: DNA
<213> ORGANISM: Artificial Sequence
<220> FEATURE:
<223> OTHER INFORMATION: In-Frame Amber Codon Fragment from Phage
      Display

<400> SEQUENCE: 25
actacttata ctggtgatta g                                             21

<210> SEQ ID NO 26
<211> LENGTH: 21
<212> TYPE: DNA
<213> ORGANISM: Artificial Sequence
<220> FEATURE:
<223> OTHER INFORMATION: In-Frame Amber Codon Fragment from Phage
      Display

<400> SEQUENCE: 26
ggttcgttgc atgttcatta g                                             21

<210> SEQ ID NO 27
<211> LENGTH: 21
<212> TYPE: DNA
<213> ORGANISM: Artificial Sequence
<220> FEATURE:
<223> OTHER INFORMATION: In-Frame Amber Codon Fragment from Phage
      Display

<400> SEQUENCE: 27
tagttgcatc cggggatgcg t                                             21

<210> SEQ ID NO 28
<211> LENGTH: 21
<212> TYPE: DNA
<213> ORGANISM: Artificial Sequence
<220> FEATURE:
<223> OTHER INFORMATION: In-Frame Amber Codon Fragment from Phage
      Display

<400> SEQUENCE: 28
tattagactg attctgatgc t                                             21
```

```
<210> SEQ ID NO 29
<211> LENGTH: 7
<212> TYPE: PRT
<213> ORGANISM: Artificial Sequence
<220> FEATURE:
<223> OTHER INFORMATION: SAP01
<220> FEATURE:
<221> NAME/KEY: MISC_FEATURE
<222> LOCATION: (2)..(2)
<223> OTHER INFORMATION: X is a Non-Canonical Amino Acid

<400> SEQUENCE: 29

Lys Xaa Asn Phe Gly Tyr Tyr
1               5

<210> SEQ ID NO 30
<211> LENGTH: 7
<212> TYPE: PRT
<213> ORGANISM: Artificial Sequence
<220> FEATURE:
<223> OTHER INFORMATION: SAP02
<220> FEATURE:
<221> NAME/KEY: MISC_FEATURE
<222> LOCATION: (5)..(5)
<223> OTHER INFORMATION: X is a Non-Canonical Amino Acid

<400> SEQUENCE: 30

Lys Trp Lys Val Xaa Thr Ser
1               5

<210> SEQ ID NO 31
<211> LENGTH: 7
<212> TYPE: PRT
<213> ORGANISM: Artificial Sequence
<220> FEATURE:
<223> OTHER INFORMATION: SAP03
<220> FEATURE:
<221> NAME/KEY: MISC_FEATURE
<222> LOCATION: (3)..(3)
<223> OTHER INFORMATION: X is a Non-Canonical Amino Acid

<400> SEQUENCE: 31

Thr Trp Xaa Lys Ser Asn Trp
1               5

<210> SEQ ID NO 32
<211> LENGTH: 7
<212> TYPE: PRT
<213> ORGANISM: Artificial Sequence
<220> FEATURE:
<223> OTHER INFORMATION: SAP04
<220> FEATURE:
<221> NAME/KEY: MISC_FEATURE
<222> LOCATION: (7)..(7)
<223> OTHER INFORMATION: X is a Non-Canonical Amino Acid

<400> SEQUENCE: 32

Met Ala Lys Pro Gln Arg Xaa
1               5

<210> SEQ ID NO 33
<211> LENGTH: 7
<212> TYPE: PRT
<213> ORGANISM: Artificial Sequence
<220> FEATURE:
<223> OTHER INFORMATION: SAP05
<220> FEATURE:
<221> NAME/KEY: MISC_FEATURE
<222> LOCATION: (6)..(6)
<223> OTHER INFORMATION: X is a Non-Canonical Amino Acid
```

```
<400> SEQUENCE: 33

Arg Glu His Lys Pro Xaa Asn
1               5

<210> SEQ ID NO 34
<211> LENGTH: 7
<212> TYPE: PRT
<213> ORGANISM: Artificial Sequence
<220> FEATURE:
<223> OTHER INFORMATION: SAP06
<220> FEATURE:
<221> NAME/KEY: MISC_FEATURE
<222> LOCATION: (3)..(3)
<223> OTHER INFORMATION: X is a Non-Canonical Amino Acid

<400> SEQUENCE: 34

Lys Leu Xaa Lys His Tyr Pro
1               5

<210> SEQ ID NO 35
<211> LENGTH: 7
<212> TYPE: PRT
<213> ORGANISM: Artificial Sequence
<220> FEATURE:
<223> OTHER INFORMATION: SAP09
<220> FEATURE:
<221> NAME/KEY: MISC_FEATURE
<222> LOCATION: (3)..(3)
<223> OTHER INFORMATION: X is a Non-Canonical Amino Acid

<400> SEQUENCE: 35

Lys Leu Xaa Lys His Tyr Pro
1               5

<210> SEQ ID NO 36
<211> LENGTH: 7
<212> TYPE: PRT
<213> ORGANISM: Artificial Sequence
<220> FEATURE:
<223> OTHER INFORMATION: SAP10
<220> FEATURE:
<221> NAME/KEY: MISC_FEATURE
<222> LOCATION: (3)..(3)
<223> OTHER INFORMATION: X is a Non-Canonical Amino Acid

<400> SEQUENCE: 36

Lys Leu Xaa Lys His Tyr Pro
1               5

<210> SEQ ID NO 37
<211> LENGTH: 7
<212> TYPE: PRT
<213> ORGANISM: Artificial Sequence
<220> FEATURE:
<223> OTHER INFORMATION: SAP11
<220> FEATURE:
<221> NAME/KEY: MISC_FEATURE
<222> LOCATION: (3)..(3)
<223> OTHER INFORMATION: X is a Non-Canonical Amino Acid

<400> SEQUENCE: 37

Lys Leu Xaa Lys His Tyr Pro
1               5

<210> SEQ ID NO 38
<211> LENGTH: 7
<212> TYPE: PRT
<213> ORGANISM: Artificial Sequence
<220> FEATURE:
```

```
<223> OTHER INFORMATION: SAP12
<220> FEATURE:
<221> NAME/KEY: MISC_FEATURE
<222> LOCATION: (3)..(3)
<223> OTHER INFORMATION: X is a Non-Canonical Amino Acid

<400> SEQUENCE: 38

Lys Leu Xaa Lys His Tyr Pro
1               5

<210> SEQ ID NO 39
<211> LENGTH: 7
<212> TYPE: PRT
<213> ORGANISM: Artificial Sequence
<220> FEATURE:
<223> OTHER INFORMATION: SAP13
<220> FEATURE:
<221> NAME/KEY: MISC_FEATURE
<222> LOCATION: (3)..(3)
<223> OTHER INFORMATION: X is a Non-Canonical Amino Acid

<400> SEQUENCE: 39

Lys His Xaa Lys Ala Ile Pro
1               5

<210> SEQ ID NO 40
<211> LENGTH: 7
<212> TYPE: PRT
<213> ORGANISM: Artificial Sequence
<220> FEATURE:
<223> OTHER INFORMATION: SAP14
<220> FEATURE:
<221> NAME/KEY: MISC_FEATURE
<222> LOCATION: (3)..(3)
<223> OTHER INFORMATION: X is a Non-Canonical Amino Acid

<400> SEQUENCE: 40

Lys Met Xaa Pro Gln Arg Asn
1               5

<210> SEQ ID NO 41
<211> LENGTH: 7
<212> TYPE: PRT
<213> ORGANISM: Artificial Sequence
<220> FEATURE:
<223> OTHER INFORMATION: SAP15
<220> FEATURE:
<221> NAME/KEY: MISC_FEATURE
<222> LOCATION: (3)..(3)
<223> OTHER INFORMATION: X is a Non-Canonical Amino Acid

<400> SEQUENCE: 41

Lys Met Xaa Pro Gln Arg Asn
1               5

<210> SEQ ID NO 42
<211> LENGTH: 7
<212> TYPE: PRT
<213> ORGANISM: Artificial Sequence
<220> FEATURE:
<223> OTHER INFORMATION: SAP16
<220> FEATURE:
<221> NAME/KEY: MISC_FEATURE
<222> LOCATION: (3)..(3)
<223> OTHER INFORMATION: X is a Non-Canonical Amino Acid

<400> SEQUENCE: 42

Lys Met Xaa Pro Gln Arg Asn
1               5
```

```
<210> SEQ ID NO 43
<211> LENGTH: 7
<212> TYPE: PRT
<213> ORGANISM: Artificial Sequence
<220> FEATURE:
<223> OTHER INFORMATION: SAP17
<220> FEATURE:
<221> NAME/KEY: MISC_FEATURE
<222> LOCATION: (3)..(3)
<223> OTHER INFORMATION: X is a Non-Canonical Amino Acid

<400> SEQUENCE: 43

Lys Met Xaa Pro Gln Arg Asn
1               5

<210> SEQ ID NO 44
<211> LENGTH: 7
<212> TYPE: PRT
<213> ORGANISM: Artificial Sequence
<220> FEATURE:
<223> OTHER INFORMATION: SAP18
<220> FEATURE:
<221> NAME/KEY: MISC_FEATURE
<222> LOCATION: (3)..(3)
<223> OTHER INFORMATION: X is a Non-Canonical Amino Acid

<400> SEQUENCE: 44

Lys Met Xaa Pro Gln Arg Asn
1               5

<210> SEQ ID NO 45
<211> LENGTH: 7
<212> TYPE: PRT
<213> ORGANISM: Artificial Sequence
<220> FEATURE:
<223> OTHER INFORMATION: SAP19
<220> FEATURE:
<221> NAME/KEY: MISC_FEATURE
<222> LOCATION: (4)..(4)
<223> OTHER INFORMATION: X is a Non-Canonical Amino Acid

<400> SEQUENCE: 45

Lys Trp Cys Xaa Asn Cys Arg
1               5

<210> SEQ ID NO 46
<211> LENGTH: 7
<212> TYPE: PRT
<213> ORGANISM: Artificial Sequence
<220> FEATURE:
<223> OTHER INFORMATION: SAP20
<220> FEATURE:
<221> NAME/KEY: MISC_FEATURE
<222> LOCATION: (6)..(6)
<223> OTHER INFORMATION: X is a Non-Canonical Amino Acid

<400> SEQUENCE: 46

Ser Ala Ala Lys Thr Xaa Ile
1               5

<210> SEQ ID NO 47
<211> LENGTH: 7
<212> TYPE: PRT
<213> ORGANISM: Artificial Sequence
<220> FEATURE:
<223> OTHER INFORMATION: S2P01
<220> FEATURE:
<221> NAME/KEY: MISC_FEATURE
<222> LOCATION: (2)..(2)
<223> OTHER INFORMATION: X is a Non-Canonical Amino Acid
```

```
<400> SEQUENCE: 47

Leu Xaa Met Thr Ser Ile Leu
1               5

<210> SEQ ID NO 48
<211> LENGTH: 7
<212> TYPE: PRT
<213> ORGANISM: Artificial Sequence
<220> FEATURE:
<223> OTHER INFORMATION: S2P02
<220> FEATURE:
<221> NAME/KEY: MISC_FEATURE
<222> LOCATION: (3)..(3)
<223> OTHER INFORMATION: X is a Non-Canonical Amino Acid

<400> SEQUENCE: 48

His Leu Xaa Thr Phe Phe Tyr
1               5

<210> SEQ ID NO 49
<211> LENGTH: 7
<212> TYPE: PRT
<213> ORGANISM: Artificial Sequence
<220> FEATURE:
<223> OTHER INFORMATION: S2P03
<220> FEATURE:
<221> NAME/KEY: MISC_FEATURE
<222> LOCATION: (4)..(4)
<223> OTHER INFORMATION: X is a Non-Canonical Amino Acid

<400> SEQUENCE: 49

Cys Thr Val Xaa Thr Ser Leu
1               5

<210> SEQ ID NO 50
<211> LENGTH: 7
<212> TYPE: PRT
<213> ORGANISM: Artificial Sequence
<220> FEATURE:
<223> OTHER INFORMATION: S2P04
<220> FEATURE:
<221> NAME/KEY: MISC_FEATURE
<222> LOCATION: (5)..(5)
<223> OTHER INFORMATION: X is a Non-Canonical Amino Acid

<400> SEQUENCE: 50

Thr Cys Thr Val Xaa Ile Gly
1               5

<210> SEQ ID NO 51
<211> LENGTH: 7
<212> TYPE: PRT
<213> ORGANISM: Artificial Sequence
<220> FEATURE:
<223> OTHER INFORMATION: S2P05
<220> FEATURE:
<221> NAME/KEY: MISC_FEATURE
<222> LOCATION: (5)..(5)
<223> OTHER INFORMATION: X is a Non-Canonical Amino Acid

<400> SEQUENCE: 51

Thr Cys Thr Val Xaa Ile Gly
1               5

<210> SEQ ID NO 52
<211> LENGTH: 7
<212> TYPE: PRT
<213> ORGANISM: Artificial Sequence
```

```
<220> FEATURE:
<223> OTHER INFORMATION: S2P06
<220> FEATURE:
<221> NAME/KEY: MISC_FEATURE
<222> LOCATION: (5)..(5)
<223> OTHER INFORMATION: X is a Non-Canonical Amino Acid

<400> SEQUENCE: 52

Thr Cys Thr Val Xaa Ile Gly
1               5

<210> SEQ ID NO 53
<211> LENGTH: 7
<212> TYPE: PRT
<213> ORGANISM: Artificial Sequence
<220> FEATURE:
<223> OTHER INFORMATION: S2P07
<220> FEATURE:
<221> NAME/KEY: MISC_FEATURE
<222> LOCATION: (4)..(4)
<223> OTHER INFORMATION: X is a Non-Canonical Amino Acid

<400> SEQUENCE: 53

Cys Thr Phe Xaa Val Pro Thr
1               5

<210> SEQ ID NO 54
<211> LENGTH: 7
<212> TYPE: PRT
<213> ORGANISM: Artificial Sequence
<220> FEATURE:
<223> OTHER INFORMATION: S2P08
<220> FEATURE:
<221> NAME/KEY: MISC_FEATURE
<222> LOCATION: (5)..(5)
<223> OTHER INFORMATION: X is a Non-Canonical Amino Acid

<400> SEQUENCE: 54

Trp Ser Gly Phe Xaa Ala Pro
1               5

<210> SEQ ID NO 55
<211> LENGTH: 7
<212> TYPE: PRT
<213> ORGANISM: Artificial Sequence
<220> FEATURE:
<223> OTHER INFORMATION: S2P09
<220> FEATURE:
<221> NAME/KEY: MISC_FEATURE
<222> LOCATION: (5)..(5)
<223> OTHER INFORMATION: X is a Non-Canonical Amino Acid

<400> SEQUENCE: 55

Trp Ser Gly Phe Xaa Ala Pro
1               5

<210> SEQ ID NO 56
<211> LENGTH: 7
<212> TYPE: PRT
<213> ORGANISM: Artificial Sequence
<220> FEATURE:
<223> OTHER INFORMATION: S2P10
<220> FEATURE:
<221> NAME/KEY: MISC_FEATURE
<222> LOCATION: (2)..(2)
<223> OTHER INFORMATION: X is a Non-Canonical Amino Acid

<400> SEQUENCE: 56

Phe Xaa Leu Glu Ser Phe Leu
1               5
```

```
<210> SEQ ID NO 57
<211> LENGTH: 7
<212> TYPE: PRT
<213> ORGANISM: Artificial Sequence
<220> FEATURE:
<223> OTHER INFORMATION: S2P11
<220> FEATURE:
<221> NAME/KEY: MISC_FEATURE
<222> LOCATION: (5)..(5)
<223> OTHER INFORMATION: X is a Non-Canonical Amino Acid

<400> SEQUENCE: 57

Ser Asn Val Phe Xaa Val Ile
1               5

<210> SEQ ID NO 58
<211> LENGTH: 7
<212> TYPE: PRT
<213> ORGANISM: Artificial Sequence
<220> FEATURE:
<223> OTHER INFORMATION: S2P12
<220> FEATURE:
<221> NAME/KEY: MISC_FEATURE
<222> LOCATION: (3)..(3)
<223> OTHER INFORMATION: X is a Non-Canonical Amino Acid

<400> SEQUENCE: 58

Ala Phe Xaa His Met Thr Val
1               5

<210> SEQ ID NO 59
<211> LENGTH: 7
<212> TYPE: PRT
<213> ORGANISM: Artificial Sequence
<220> FEATURE:
<223> OTHER INFORMATION: S2P13
<220> FEATURE:
<221> NAME/KEY: MISC_FEATURE
<222> LOCATION: (5)..(5)
<223> OTHER INFORMATION: X is a Non-Canonical Amino Acid

<400> SEQUENCE: 59

Gln Met Arg Phe Xaa Pro Ile
1               5

<210> SEQ ID NO 60
<211> LENGTH: 7
<212> TYPE: PRT
<213> ORGANISM: Artificial Sequence
<220> FEATURE:
<223> OTHER INFORMATION: S2P14
<220> FEATURE:
<221> NAME/KEY: MISC_FEATURE
<222> LOCATION: (5)..(5)
<223> OTHER INFORMATION: X is a Non-Canonical Amino Acid

<400> SEQUENCE: 60

Gln Met Arg Phe Xaa Pro Ile
1               5

<210> SEQ ID NO 61
<211> LENGTH: 7
<212> TYPE: PRT
<213> ORGANISM: Artificial Sequence
<220> FEATURE:
<223> OTHER INFORMATION: S2P15
<220> FEATURE:
<221> NAME/KEY: MISC_FEATURE
<222> LOCATION: (1)..(1)
```

```
<223> OTHER INFORMATION: X is a Non-Canonical Amino Acid

<400> SEQUENCE: 61

Xaa Val Cys Ser Cys Tyr Ala
1               5

<210> SEQ ID NO 62
<211> LENGTH: 7
<212> TYPE: PRT
<213> ORGANISM: Artificial Sequence
<220> FEATURE:
<223> OTHER INFORMATION: S2P16
<220> FEATURE:
<221> NAME/KEY: MISC_FEATURE
<222> LOCATION: (1)..(1)
<223> OTHER INFORMATION: X is a Non-Canonical Amino Acid

<400> SEQUENCE: 62

Xaa Val Cys Ser Cys Tyr Ala
1               5

<210> SEQ ID NO 63
<211> LENGTH: 7
<212> TYPE: PRT
<213> ORGANISM: Artificial Sequence
<220> FEATURE:
<223> OTHER INFORMATION: S2P17
<220> FEATURE:
<221> NAME/KEY: MISC_FEATURE
<222> LOCATION: (5)..(5)
<223> OTHER INFORMATION: X is a Non-Canonical Amino Acid

<400> SEQUENCE: 63

Cys Trp Trp Cys Xaa Val Ser
1               5

<210> SEQ ID NO 64
<211> LENGTH: 7
<212> TYPE: PRT
<213> ORGANISM: Artificial Sequence
<220> FEATURE:
<223> OTHER INFORMATION: S2P18
<220> FEATURE:
<221> NAME/KEY: MISC_FEATURE
<222> LOCATION: (6)..(6)
<223> OTHER INFORMATION: X is a Non-Canonical Amino Acid

<400> SEQUENCE: 64

Thr Glu Ser Asn His Xaa Gly
1               5

<210> SEQ ID NO 65
<211> LENGTH: 7
<212> TYPE: PRT
<213> ORGANISM: Artificial Sequence
<220> FEATURE:
<223> OTHER INFORMATION: S2P19
<220> FEATURE:
<221> NAME/KEY: MISC_FEATURE
<222> LOCATION: (7)..(7)
<223> OTHER INFORMATION: X is a Non-Canonical Amino Acid

<400> SEQUENCE: 65

Leu Phe Leu Trp Met Pro Xaa
1               5

<210> SEQ ID NO 66
<211> LENGTH: 7
<212> TYPE: PRT
```

```
<213> ORGANISM: Artificial Sequence
<220> FEATURE:
<223> OTHER INFORMATION: S2P20
<220> FEATURE:
<221> NAME/KEY: MISC_FEATURE
<222> LOCATION: (4)..(4)
<223> OTHER INFORMATION: X is a Non-Canonical Amino Acid

<400> SEQUENCE: 66

Ser Pro Met Xaa Asn Lys Val
1               5

<210> SEQ ID NO 67
<211> LENGTH: 7
<212> TYPE: PRT
<213> ORGANISM: Artificial Sequence
<220> FEATURE:
<223> OTHER INFORMATION: ENL Inhibitor
<220> FEATURE:
<221> NAME/KEY: MISC_FEATURE
<222> LOCATION: (6)..(6)
<223> OTHER INFORMATION: X is CrK

<400> SEQUENCE: 67

Asp Ile Trp Cys Phe Xaa Gly
1               5

<210> SEQ ID NO 68
<211> LENGTH: 7
<212> TYPE: PRT
<213> ORGANISM: Artificial Sequence
<220> FEATURE:
<223> OTHER INFORMATION: ENL Inhibitor
<220> FEATURE:
<221> NAME/KEY: MISC_FEATURE
<222> LOCATION: (2)..(2)
<223> OTHER INFORMATION: X is CrK

<400> SEQUENCE: 68

Ser Xaa Asp Ile Trp Cys Phe
1               5
```